(12) United States Patent
Mikszta et al.

(10) Patent No.: US 7,473,247 B2
(45) Date of Patent: Jan. 6, 2009

(54) INTRADERMAL DELIVERY OF VACCINES AND GENE THERAPEUTIC AGENTS VIA MICROCANNULA

(75) Inventors: John A. Mikszta, Durham, NC (US); Jason B. Alarcon, Durham, NC (US); Cheryl Dean, Raleigh, NC (US); Andrea Waterston, Holly Springs, NC (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 880 days.

(21) Appl. No.: 10/679,038

(22) Filed: Oct. 2, 2003

(65) Prior Publication Data

US 2004/0131641 A1    Jul. 8, 2004

Related U.S. Application Data

(63) Continuation-in-part of application No. 10/185,717, filed on Jul. 1, 2002, now abandoned, which is a continuation-in-part of application No. 10/044,504, filed on Jan. 10, 2002, now abandoned, which is a continuation-in-part of application No. 09/834,438, filed on Apr. 13, 2001, now Pat. No. 6,843,781, and a continuation-in-part of application No. 09/835,243, filed on Apr. 13, 2001, now Pat. No. 6,569,143, which is a continuation-in-part of application No. 09/417,671, filed on Oct. 14, 1999, now Pat. No. 6,494,865.

(60) Provisional application No. 60/301,476, filed on Jun. 29, 2001.

(51) Int. Cl.
*A61M 31/00* (2006.01)

(52) U.S. Cl. .................................. 604/507

(58) Field of Classification Search ................. 606/167, 606/168, 169, 170–174, 192–194, 890.1; 604/22, 271, 115–117, 272, 191, 164.01–164.02, 604/165.01, 158, 159, 264, 506–511
See application file for complete search history.

(56) References Cited

U.S. PATENT DOCUMENTS

| 1,274,081 A | 7/1918 | Riethmueller |
| 1,439,707 A | 11/1922 | Gaschke |
| 1,934,046 A | 11/1933 | Demarchi |
| 2,559,474 A | 7/1951 | Son |
| 2,569,901 A | 10/1951 | Richard |
| 2,619,962 A | 12/1952 | Rosenthal |

(Continued)

FOREIGN PATENT DOCUMENTS

CA    2 349 431    5/2000

(Continued)

OTHER PUBLICATIONS

U.S. Appl. No. 09/606,909, filed Jun. 29, 2000, Pettis et al.

(Continued)

*Primary Examiner*—Manuel A Mendez
(74) *Attorney, Agent, or Firm*—Alston & Bird LLP

(57) ABSTRACT

The present invention relates to methods and devices for administration of vaccines and gene therapeutic agents into the intradermal layer of skin.

6 Claims, 11 Drawing Sheets

U.S. PATENT DOCUMENTS

| | | | |
|---|---|---|---|
| 2,876,770 A | 3/1959 | White | |
| 3,073,306 A | 1/1963 | Linder | |
| 3,400,715 A | 9/1968 | Pederson | |
| 3,814,097 A | 6/1974 | Ganderton et al. | |
| 3,890,971 A | 6/1975 | Leeson et al. | |
| 3,964,482 A | 6/1976 | Gerstel et al. | |
| 4,060,073 A | 11/1977 | Collica et al. | |
| 4,270,537 A | 6/1981 | Romaine | |
| 4,373,526 A | 2/1983 | Kling | |
| 4,468,223 A | 8/1984 | Minagawa et al. | |
| 4,583,978 A | 4/1986 | Porat et al. | |
| 4,592,753 A | 6/1986 | Panoz | |
| 4,596,556 A | 6/1986 | Morrow et al. | |
| 4,769,003 A | 9/1988 | Stamler | |
| 4,774,948 A | 10/1988 | Markham | |
| 4,790,824 A | 12/1988 | Morrow et al. | |
| 4,826,687 A | 5/1989 | Nerome et al. | |
| 4,834,704 A | 5/1989 | Reinicke | |
| 4,883,573 A | 11/1989 | Voss et al. | |
| 4,886,499 A | 12/1989 | Cirelli et al. | |
| 4,898,588 A | 2/1990 | Roberts | |
| 4,940,460 A | 7/1990 | Casey, I. et al. | |
| 4,941,880 A | 7/1990 | Burns | |
| 4,955,871 A | 9/1990 | Thomas | |
| 4,978,344 A | 12/1990 | Dombrowski et al. | |
| 5,003,987 A | 4/1991 | Grinwald | |
| 5,015,235 A | 5/1991 | Crossman | |
| 5,064,413 A | 11/1991 | McKinnon et al. | |
| 5,071,353 A | 12/1991 | van der Wal | |
| 5,098,389 A | 3/1992 | Cappucci | |
| 5,137,516 A | 8/1992 | Rand et al. | |
| 5,141,496 A | 8/1992 | Dalto et al. | |
| 5,147,328 A | 9/1992 | Dragosits et al. | |
| 5,156,591 A | 10/1992 | Gross et al. | |
| 5,190,521 A | 3/1993 | Hubbard et al. | |
| 5,195,526 A | 3/1993 | Michelson | |
| 5,222,949 A | 6/1993 | Kaldany | |
| 5,250,023 A | 10/1993 | Lee et al. | |
| 5,279,544 A | 1/1994 | Gross et al. | |
| 5,279,552 A | 1/1994 | Magnet | |
| 5,292,506 A | 3/1994 | Oki et al. | |
| 5,312,335 A | 5/1994 | McKinnon et al. | |
| 5,331,954 A | 7/1994 | Rex et al. | |
| 5,334,144 A | 8/1994 | Alchas et al. | |
| 5,339,163 A | 8/1994 | Homma et al. | |
| 5,368,578 A | 11/1994 | Covington et al. | |
| 5,383,851 A | 1/1995 | McKinnon, Jr. et al. | |
| 5,417,662 A | 5/1995 | Hjertman et al. | |
| 5,431,155 A | 7/1995 | Marelli | |
| 5,437,647 A | 8/1995 | Firth et al. | |
| 5,466,220 A | 11/1995 | Brenneman | |
| 5,480,381 A | 1/1996 | Weston | |
| 5,496,286 A | 3/1996 | Stiehl et al. | |
| 5,503,627 A | 4/1996 | McKinnon et al. | |
| 5,514,107 A | 5/1996 | Haber et al. | |
| 5,520,639 A | 5/1996 | Peterson et al. | |
| 5,527,288 A | 6/1996 | Gross et al. | |
| 5,569,189 A | 10/1996 | Parsons | |
| 5,578,014 A | 11/1996 | Erez et al. | |
| 5,582,591 A | 12/1996 | Cheikh | |
| 5,582,598 A | 12/1996 | Chanoch | |
| 5,591,139 A | 1/1997 | Lin et al. | |
| 5,599,302 A | 2/1997 | Lilley et al. | |
| 5,649,912 A | 7/1997 | Peterson | |
| 5,665,071 A | 9/1997 | Wyrick | |
| 5,672,883 A | 9/1997 | Reich | |
| 5,697,901 A | 12/1997 | Eriksson | |
| 5,702,362 A | 12/1997 | Herold et al. | |
| 5,702,717 A | 12/1997 | Cha et al. | |
| 5,704,911 A | 1/1998 | Parsons | |
| 5,779,677 A | 7/1998 | Frezza | |
| 5,800,420 A | 9/1998 | Gross et al. | |
| 5,801,057 A | 9/1998 | Smart et al. | |
| 5,820,622 A | 10/1998 | Gross et al. | |
| 5,830,463 A * | 11/1998 | Duke et al. | 424/93.51 |
| 5,848,990 A | 12/1998 | Cirelli et al. | |
| 5,848,991 A | 12/1998 | Gross et al. | |
| 5,861,174 A | 1/1999 | Stratton et al. | |
| 5,873,856 A | 2/1999 | Hjertman et al. | |
| 5,876,582 A | 3/1999 | Frazier | |
| 5,879,326 A | 3/1999 | Godshall et al. | |
| 5,879,327 A | 3/1999 | Moreau DeFarges et al. | |
| 5,891,085 A | 4/1999 | Lilley et al. | |
| 5,893,397 A | 4/1999 | Peterson et al. | |
| 5,912,000 A | 6/1999 | Podolski et al. | |
| 5,921,963 A | 7/1999 | Erez et al. | |
| 5,928,207 A | 7/1999 | Pisano et al. | |
| 5,944,700 A | 8/1999 | Nguyen et al. | |
| 5,957,895 A | 9/1999 | Sage et al. | |
| 5,957,897 A | 9/1999 | Jeffrey | |
| 5,961,495 A | 10/1999 | Walters et al. | |
| 5,993,412 A | 11/1999 | Deily et al. | |
| 5,997,501 A | 12/1999 | Gross et al. | |
| 6,001,089 A | 12/1999 | Burroughs et al. | |
| 6,004,299 A | 12/1999 | Arai et al. | |
| 6,007,821 A | 12/1999 | Srivastava et al. | |
| 6,036,675 A | 3/2000 | Thorne et al. | |
| 6,053,893 A | 4/2000 | Bucher | |
| 6,056,716 A | 5/2000 | D'Antonio et al. | |
| 6,083,197 A | 7/2000 | Umbaugh | |
| 6,090,077 A | 7/2000 | Shaw | |
| 6,090,080 A | 7/2000 | Jost et al. | |
| 6,090,082 A | 7/2000 | King et al. | |
| 6,093,170 A | 7/2000 | Hsu et al. | |
| 6,099,504 A | 8/2000 | Gross et al. | |
| 6,112,743 A | 9/2000 | Denton | |
| 6,136,606 A | 10/2000 | Chatfield | |
| 6,200,291 B1 | 3/2001 | Di Pietro | |
| 6,210,369 B1 | 4/2001 | Wilmot et al. | |
| 6,213,977 B1 | 4/2001 | Hjertman et al. | |
| 6,309,650 B1 * | 10/2001 | Kim et al. | 424/218.1 |
| 6,319,224 B1 | 11/2001 | Stout et al. | |
| 6,319,230 B1 * | 11/2001 | Palasis et al. | 604/164.01 |
| 6,334,856 B1 | 1/2002 | Allen et al. | |
| 6,346,095 B1 | 2/2002 | Gross et al. | |
| 6,361,524 B1 * | 3/2002 | Odell et al. | 604/187 |
| 6,372,223 B1 | 4/2002 | Kistner et al. | |
| 6,482,176 B1 | 11/2002 | Wich | |
| 6,485,729 B1 | 11/2002 | Smith et al. | |
| 6,494,865 B1 | 12/2002 | Alchas | |
| 6,503,231 B1 * | 1/2003 | Prausnitz et al. | 604/272 |
| 6,525,030 B1 * | 2/2003 | Eriksson | 514/44 |
| 6,534,065 B1 | 3/2003 | Makin et al. | |
| 6,537,242 B1 | 3/2003 | Palmer | |
| 6,569,123 B2 | 5/2003 | Alchas et al. | |
| 6,569,143 B2 | 5/2003 | Alchas et al. | |
| 6,623,457 B1 * | 9/2003 | Rosenberg | 604/191 |
| 6,776,776 B2 | 8/2004 | Alchas et al. | |
| 6,808,506 B2 * | 10/2004 | Lastovich et al. | 604/47 |
| 7,078,500 B1 * | 7/2006 | Wands et al. | 536/23.1 |
| 2002/0025326 A1 | 2/2002 | Blonder et al. | |
| 2002/0095134 A1 | 7/2002 | Pettis et al. | |
| 2002/0198509 A1 | 12/2002 | Mikszta et al. | |
| 2003/0073609 A1 | 4/2003 | Pinkerton | |
| 2003/0093040 A1 | 5/2003 | Mikszta et al. | |
| 2004/0028707 A1 | 2/2004 | Pinkerton | |
| 2004/0073160 A1 | 4/2004 | Pinkerton | |
| 2004/0082934 A1 | 4/2004 | Pettis et al. | |
| 2004/0120964 A1 | 6/2004 | Mikszta et al. | |
| 2004/0131641 A1 | 7/2004 | Mikszta et al. | |
| 2004/0170654 A1 | 9/2004 | Pinkerton | |
| 2004/0175401 A1 | 9/2004 | Pinkerton | |
| 2005/0008683 A1 | 1/2005 | Mikszta et al. | |
| 2005/0096330 A1 | 5/2005 | Pettis et al. | |

| | | | |
|---|---|---|---|
| 2005/0096331 | A1 | 5/2005 | Pettis et al. |
| 2005/0096332 | A1 | 5/2005 | Pettis et al. |
| 2005/0123550 | A1 | 6/2005 | Laurent et al. |
| 2005/0180952 | A1 | 8/2005 | Pettis et al. |
| 2005/0181033 | A1 | 8/2005 | Dekker et al. |
| 2005/0196380 | A1 | 9/2005 | Mikszta et al. |
| 2005/0255121 | A1 | 11/2005 | Campbell et al. |
| 2005/0281832 | A1 | 12/2005 | Campbell et al. |

FOREIGN PATENT DOCUMENTS

| | | |
|---|---|---|
| DE | 41 27 887 C1 | 1/1993 |
| DE | 29918794 | 2/2000 |
| EP | 02 79583 | 10/1993 |
| EP | 0 429 842 | 8/1996 |
| EP | 0 904 790 A2 | 3/1999 |
| EP | 1066848 | 1/2001 |
| EP | 1 086 718 | 3/2001 |
| EP | 1 086 719 | 3/2001 |
| EP | 1 088 642 | 4/2001 |
| EP | 1 092 444 A | 4/2001 |
| FR | 2 612 401 A1 | 9/1988 |
| GB | 725024 | 3/1955 |
| GB | 735538 | 8/1955 |
| GB | 2 206 794 A1 | 1/1989 |
| JP | 2000-37456 | 2/2000 |
| WO | WO 9309826 | 5/1993 |
| WO | WO 94/23777 | 10/1994 |
| WO | WO 95/01198 | 1/1995 |
| WO | WO 96/17648 | 6/1996 |
| WO | WO 96/37155 | 11/1996 |
| WO | WO 96/37256 | 11/1996 |
| WO | WO 97/13537 | 4/1997 |
| WO | WO 97/21457 | 6/1997 |
| WO | WO 97/37705 | 10/1997 |
| WO | WO 97/47323 | 12/1997 |
| WO | WO 98/03196 | 1/1998 |
| WO | WO 98/42374 | 10/1998 |
| WO | WO 9925402 | 5/1999 |
| WO | WO 99/27986 | 6/1999 |
| WO | WO 99/34850 | 7/1999 |
| WO | WO 9937345 | 7/1999 |
| WO | WO 99/43350 | 9/1999 |
| WO | WO 99/64580 | 12/1999 |
| WO | WO 00/09186 | 2/2000 |
| WO | WO 00/29016 | 5/2000 |
| WO | WO 00/54839 | 9/2000 |
| WO | WO 0056384 | 9/2000 |
| WO | WO 00/67647 | 11/2000 |
| WO | WO 00/74763 | 12/2000 |
| WO | WO 01/35994 | 5/2001 |
| WO | WO 01/80866 | 11/2001 |
| WO | WO 01/98206 | 12/2001 |
| WO | WO 02/02179 A | 1/2002 |
| WO | WO 02/11669 | 2/2002 |
| WO | WO 02/32454 A | 4/2002 |
| WO | WO 02/62321 | 8/2002 |
| WO | WO 02/067983 A | 9/2002 |
| WO | WO 02/074336 A | 9/2002 |
| WO | WO 02/083216 A | 10/2002 |
| WO | WO 02/083232 | 10/2002 |
| WO | WO 02/087494 A | 11/2002 |
| WO | WO 03/002069 | 1/2003 |
| WO | WO 03/002175 | 1/2003 |

OTHER PUBLICATIONS

U.S. Appl. No. 11/006,086, filed Dec. 6, 2004, Campbell et al.
"Flu vaccine: skin injection method effective in younger people," *American Health Line: Research Notes* (Nov. 4, 2004).
Alpar et al., "Intranasal vaccination against plague, tetanus and diphtheria," *Advanced Drug Delivery Reviews* 51:173-201 (2001).
Autret, et al., Comparison of Pharmacokinetics and tolerance of Calcitonine administered by Intradermal or Subcutaneous Route, Fundamental Clinical Pharmacology, vol. 3, No. 2, pp. 170-171, 1989.
Autret, et al, [Comparison of plasma concentration and tolerance of a single dose of human calcitonin by intradermal and subcutaneous administration], Therapie 46(1):5-8, 1991.
Bader et al., Influenza vaccine experience in Seattle. Am. J. Public Health. May 1980;70(5):545.
Baldrick, 2000, "Pharmaceutical excipient development: The need for preclinical guidance," Regulatory Toxicology Pharmacol. 32:210-218.
Belshe et al., "Serum antibody responses after intradermal vaccination against influenza," New England Journal of Medicine 351(22):2286-2294 (2004).
Benoni, et al., Distribution of Ceftazidime in Ascitic Fluid, Antimicrobial Agents and Chemotherapy, vol. 25, No. 6, Jun. 1984, pp. 760-763.
Bickers, et al., editors, Clinical Pharmacology of Skin Disease, pp. 57-90, Churchill Livingstone, Inc. 1984.
Blonder et al., 1999, "Dose-dependent hyperlipidemia in rabbits following administration of poloxamer 407 gel," Life Sci. 65(21):PL261-266.
Bocci, et al., The Lymphatic Route. IV. Pharmacokinetics of Human Recombinant Interferon a2 and Natural Interferon beta Administered Intradermally in Rabbits, International Journal of Pharmaceutics, 32, 1986, pp. 103-110 Elsevier Science Publishers B.V. (Biomedical Division).
Branswell, "Vaccine stretching may be an option for future shortages, pandemics: studies," *Canadian Press News Wire* (Nov. 3, 2004).
Bressolle, et al., A Weibull Distribution Model for Intradermal Administration of Ceftazidime, Journal of Pharmaceutical Sciences, vol. 82, No. 11, Nov. 1993, pp. 1175-1178.
Bronaugh et al., Methods for in Vitro Percutaneous Absorption Studies. II. Animal Models for Human Skin. Toxicol Appl. Pharmacol. Mar. 15, 1982;62(3):481-8.
Brooks, et al., Intradermal administration of bivalent and monovalent influenza vaccines. Ann. Allergy. Aug. 1977; 39(2):110-2.
Brown, et al., The immunizing effects of influenza A/New Jersey/76 (Hsw1N1) virus vaccine administered intradermally and intramuscularly to audits. J. Infect. Dis. Dec. 1977;136 Suppl:S466-71.
Brukoth, et al., Transdermal and Transmucosal Powered Drug Delivery, Critical Review™ in Therapeutic Drug Carrier Systems, 16 (4), (1999), pp. 331-384.
Callen, Intralesional Corticosteriods, Journal of the American Academy of Dermatology, University of Louisville School of Medicine, pp. 149-151, 1981.
Carlsson et al., "Hepatitis A Vaccination by Intracutaneous Low Dose Administration: A less Expensive Alternative," Scand J Infect Dis; 1996;28(5):435-8.
Chaloupka et al., "Comparative Analysis of Six European Influenza Vaccines," Eur J Clin Microbiol Infect Dis; Feb. 1996;15(2):121-7.
Chatelet et al., "Clinical Immunogenicity And Tolerance Studies Of Liquid Vaccines Delivered By Jet-Injector And A New Single-Use Cartridge (Imule®): Comparison With Standard Syringe Injection," Vaccine; 1997;15(4).
Chin et al., 1996, "Manipulating systemic and mucosal immune responses with skin-deliverable adjuvants," J. Biotechnol. 44:13-19.
Chin et al., 1993, "Manipulating mucosal immune response by intradermal immunization," J. Cell. Biochem. Supp. 17C:54, Abstract HZ 111.
Chin et al., 1992, "Relationship between the immune response of sheep and the population dynamics of bacteria isolated from fleecerot lesions," Veterinary Microbiology 32:63-74.
Christodoulides et al., "Effect of adjuvant composition on immune response to a multiple antigen peptide (MAP) containing a protective epitope from *Neisseria meningitidis* class 1 porin," *Vaccine* 18:131-139 (2000).
Clark et al., "Polyvalent influenza vaccine: comparison of jet injection with intradermal and subcutaneous syringe methods of administration," Oklahoma City, Oklahoma.
Coeshott et al., 2001, "A novel adjuvant formulation containing a block copolymer with reverse gelation characteristics elicits long lasting IgG antibody responses after a single injection in mice," Abstracts of Submitted Papers, Fourth Ann. Conference Abstract S26.

Corbo M., et al, Transdermal Controlled Delivery of Propranolol from a Multilaminate Adhesive Device. Pharm Res. Sep. 1989;6(9):753-8.

Cossum, et al. Disposition of the C-Labeled Phosphorothioate Oligonucleotide ISIS 2105 after Intravenous Administration to Rats, The Journal of Pharmacology and Experimental Therapeutics, pp. 1181-1190, vol. 267, No. 3, 1993.

Cossum, et al., Pharmacokinetics of C-Labeled Phosphorothioate Oligonucleotide, ISIS 2105 after Administration to Rats, The Journal of Pharmacology and Experimental Therapeutics, pp. 89-94, vol. 269, No. 1, 1994.

Couvreur et al., "Multiple emulsion technology for the design of microspheres containing peptides and oligopeptides," *Advanced Drug Delivery Review* 28:85-96 (1997).

Crooke, et al., A Pharmacokinetic Evaluation of C-Labled Afovirsen Sodium in Patients with Genial Warts, Clinical Pharmacology & Therapeutics, pp. 641-646, vol. 56, No. 6, Part 1, Dec. 1994.

Crowe, Experimental comparison of intradermal and subcutaneous vaccination with influenza vaccine. Am. J. Med. Technol. Nov.-Dec., 1965;31(6):387-96.

De Souza et al., "A novel adjuvant for use with a blood-stage malaria vaccine," *Vaccine* 13(14):1316-1319 (1995).

De Souza et al., "Cytokines and antibody subclass associated with protective immunity against blood-stage malaria in mice vaccinated with the C terminus of merozoite surface protein 1 plus a novel adjuvant," *Infection and Immunity* 64(9):3532-3536 (1996).

Dowdle et al., "Influenza immunization policies and practices in Japan," J Infect Dis; Feb. 1980;141(2):258-64.

Efficacy of Intradermally Administered A2 Hong Kong Vaccine, JAMA; Jul. 6, 1970;213(1).

Firooz, et al., Benefits and Risks of Intralesional Corticosteroid Injection in the Treatment of Dermatological Disease, pp. 363-370, vol. 20, No. 5, Clinical and Experimental Dermatology, Blackwell Science Ltd, Sep. 1995.

Fjerstad, "U. Minnesota proffessor uses alternative flu vaccine technique," *FSView & Florida Flambeau via U-Wire* (Nov. 15, 2004).

Flynn et al., "Influence of Needle Gauge in Mantoux Skin Testing," Chest; Nov. 1994;106(5):1463-5.

Foy, et al., Efficacy of intradermally administered A2 Hong Kong vaccine. JAMA. Jul. 6, 1970;213(1):130.

Glenn, et al., Advances in vaccine delivery: transcutaneous immunisation. Exp. Opin. Invest. Drugs 1999, 8(6):797-805.

Goodarzi, et al., Organ Distribution and Stability of Phosphorthioated Oligodeoxyribonucleotides in Mice, Biopharmaceutics & Drug Disposition, pp. 221-227, vol. 13, No. 3, John Wiley & Sons Ltd., Apr. 1992.

Gramzinski, et al., Immune response to a hepatitis B DNA vaccine in Aotus monkeys: a comparison of vaccine formulation, route method of administration. Mol. Med. Feb. 1998;4(2):109-18.

Haas et al., 2002, "Developments in the area of bioadhesive drug delivery systems," Expert Opin. Biol. Ther, 2(3):287-298.

Halperin, et al., A comparison of the intradermal and subcutaneous routes of influenza vaccination with A/New Jersey/76 (swine flu) and A/Victoria/75: report of a study and review of the literature. Am. J. Public Health. Dec. 1979;69(12):1247-50.

Haynes, et al., Ultra-long-duration Local Anesthesia Produced by Injection of Lecithin-coated Methoxyflurane Microdroplets, Anestheiology, vol. 63, vol. 5. pp. 490-499, Nov. 1985.

Henderson et al., "Comparison of higherddose Intradermal Hepatitis B Vaccination to Standard Intramuscular Vaccination of Healthcare Workers," Infect Control Hosp Epidemiol; Apr. 2000;21(4):264-9.

Henry, et al., Microfabricated Microneedles: A Novel Approach to Transdermal Drug Delivery, Journal of Pharmaceutical Sciences, vol. 87, No. 8, Aug. 1998, pp. 922-925.

Herbert, et al., Comparison of responses to influenza A/New Jersey/76-A/Victoria/75 virus vaccine administered intradermally or subcutaneously to adults with chronic respiratory disease. J. Infect. Dis. Aug. 1979;140(2):234-8.

Hunter et al., 1981, "The adjuvant activity on nonionic block polymer surfactants. I. The role of hydrophile-lipophile balance," J. Immunol. 127(3):1244-1250.

Hunter et al., 1984, "The adjuvant activity of nonionic block polymer surfactants. II. Antibody formation and inflammation related to the structure of triblock and octablock copolymers," J. Immunol. 133(6):3167-3175.

Hunter et al., 1986, "The adjuvant activity of nonionic block polymer surfactants. III. Characterization of selected biologically active surfactants," Scand. J. Immunol. 23(3):287-300.

Hunter et al., 1991, "Adjuvant activity of nonionic block copolymers. IV. Effect of molecular weight and formulation of titer and isotype of antibody," Vaccine 9:250-256.

Hunter et al., 1994, "Mechanisms of action of nonionic block copolymer adjuvants," AIDS Res. Hum. Retroviruses 10(Supp. 2):S95-98.

Hunter et al., 1995, "Copolymer adjuvant and titermax," in Des Stewart-Tull (ed.), The Theory and Practical Application of Adjuvants, John Wiley and Sons, New York pp. 51-94.

Iida et al., 1987, "Stimulation of non-specific host resistance against Sendai virus and *E. coli* infections by chitin derivatives in mice," Vaccine 5(4):270-274.

Illum, 1998, "Chitosan and its use as a pharmaceutical excipient," Pharmaceutical Res. 15(9):1326-1331.

Injection Technique Intradermal.

International Search Report dated Dec. 20, 2001 for International Appln. No. PCT/US01/12251.

International Search Report dated Dec. 20, 2001 for International Appln. No. PCT/US01/12247.

International Search Report dated Dec. 20, 2001 for International Appln. No. PCT/US01/12248.

Jabbal-Gill et al., "Stimulation of mucosal and systemic antibody responses against *Bordetella pertussis* filamentous haemagglutinin and recombinant pertussis toxin after nasal administration with chitosan in mice," Vaccine 16(20):2039-2046 (1998).

Jakobson et al., Variations in the Blood Concentration of 1,1,2-Tricholoroethane by Percutaneous Absorption and Other Routes of Administration in the Guinea Pig, vol. 41, No. 5, pp. 497-506, Acta Pharmacologizca. et Toxicologica, Nov. 1997.

Jarratt, et al., The Effects of Intradermal Steroids on the Pituitary-Adrenal Axis and the Skin, The Journal of Investigative Dermatology, vol. 62, No. 4, pp. 463-466, 1974.

Kabanov et al., "Pluronic® block copolymers: novel functional molecules for gene therapy," Advanced Drug Delivery Reviews 54:223-233 (2002).

Katz et al., 2000, "A nonionic block co-polymer adjuvant (CRL1005) enhances the immunogenicity and protective effecacy of inactivated influenza vaccine in young and aged mice," Vaccine 18(21):2177-2187.

Kaushik, et al., Transdermal Protein Delivery Using Microfabricated Microneedles, Oct/Nov. 1999 (1 page).

Ke et al., 1997, "Nonionic triblock copolymers facilitate delivery of exogenous proteins into the MHC class I and class II processing pathways," Cell Immunol. 176(2):113-121.

Keele et al., "Monographs of the Physiological Society No. 12: Substances Producing Pain and Itch," The Williams & Wilkins Company; 1964.

Kenney et al., "Dose sparing with intradermal injection of influenza vaccine," New England Journal of Medicine 351(22):2295-2301 (2004).

Kerr, "Intradermal rabies vaccine more effective," Trends Microbiol, 2001;9(9):415.

Kidane et al., "Effects of cellulose derivatives and poly(ethylene oxide) - poly(propylene oxide) tri-block copolymers (Pluronic® surfactants) on the properties of alginate based microspheres and their interactions with phagocytic cells," Journal of Controlled Release 85:181-189 (2002).

Kim et al., "Temperature-responsive and degradable hyaluronic acid/pluronic hydrogels for controlled release of human growth hormone," Journal of Controlled Release 80:69-77 (2002).

Kirpatrick, et al., Local Anesthetic Efficacy of Methoxyflurane Microdroplets in Man, vol. 67, No. 3A, Anesthesiology, Sep. 1987.

Knox et al. "New research shows intradermal rather than intramuscular vaccine injection could stretch flu vaccine supplies," *National Public Radio: All Things Considered* (Nov. 3, 2004).

Kohn, "Flu shot technique yields more doses, studies find; critics say injecting skin rather than muscle is too difficult for common use," *The Baltimore Sun: Telegraph 3A* (Nov. 4, 2004).

Lanier et al., 1999, "Peptide vaccination using nonionic block copolymers induces protective anti-viral CTL responses," Vaccine 18(5-6):549-557.

Leroy, et al., Pharmacokinetics of Ceftazidime in Normal and Uremic Subjects, Antimicrobal Agents and Chemotherapy, vol. 25, No. 5, pp. 638-642, May 1984.

Majeski et al., "Technique could stretch vaccine; changing the way shots are given means the current supply of flu vaccine could immunize 10 times as many people, two Minnesota physicians say" Saint Paul Pioneer Press: Main 1A (Oct. 27, 2004).

Majeski, "Alternate flu shot less effective in elderly; doctors proposed method to stretch vaccine supply," *Saint Paul Pioneer Press: Main* 17A (Nov. 4, 2004).

Marks et al., "Intradermal Influenza Immunization, Experience with Hong Kong Vaccine," Am Rev Respir Dis; Apr. 1971;103(4):579-81.

McAllister, et al., Solid and Hollow Microneedles for Transdermal Protein Delivery, Proceed. Int'l. Symp. Control. Rel. Bioact. Mater., 26 (Revised Jul. 1999) Controlled Release Society, Inc. pp. 192-193.

McAllister, et al., Three-Dimensional Hollow Microneedle and Microtube Arrays, Conference: Solid-State Sensors and Actuators Transducers-Conference, 1999;10th, vol. 12., pp. 1098-1103.

McConnell, "Clinical Do's & Don'ts—Giving Intradermal Injections".

McElroy, et al., Response to intradermal vaccination with A2, Hong Kong variant, influenza vaccine. N. Engl. J. Med. Nov. 6, 1969;281(19):1076.

McGugan, et al., Adrenal Suppression from Intradermal Triamcinolone. The Journal of Investigative Dermatology, vol. 40, pp. 271-272, Baltimore, MD., 1963.

McNeela et al., "Manipulating the immune system: humoral versus cell-mediated immunity," *Advanced Drug Delivery Reviews* 51:43-54 (2001).

Merriam-Webster's Collegiate Dictionary, 10$^{th}$ Edition, 1998, Merriam-Webster, Inc., Springfield, MA, p. 306.

Moghimi et al., "Poloxamers and poloxamines in nanoparticle engineering and experimental medicine," *Tibtech* 18:412-420 (2000).

Moghimi et al., 1996, "Poloxamer-188 revisited: a potentially valuable immune modulator," J. Natl. Cancer Inst. 88(11):766-768.

Montagne et al., "Intradermal influenza vaccination—can less be more?" New England Journal of Medicine 351(22):2330-2332 (2004).

Murillo et al., "Modulation of the cellular immune response after oral or subcutaneous immunization with microparticles containing *Brucella ovis* antigens," *Journal of Controlled Release* 85:237-246 (2002).
Nagafuchi et al., "Intradermal Administration of Viral Vaccines," Rev Med Virol; Apr. 1998;8(2):97-111 (Abstract).
Newman et al., 1998, "Design and development of adjuvant-active nonionic block copolymers," J. Pharm. Sci. 87(11):1357-1362.
Newman et al., 1998, Development of adjuvant-active nonionic block copolymers, Adv. Drug Deliv. Rev. 32(3):199-223.
Newman et al., 1998, "Use of nonionic block copolymers in vaccines and therapeutics," Crit. Rev. Ther. Drug Carrier Syst. 15(2):89-142.
Newman et al., 1997, "Increasing the immunogenicity of a trivalent influenza vaccine with adjuvant active nonionic block copolymers for potential use in elderly," Mech. Ageing Dev. 93:189-203.
Nickoloff, "Dermal Immune System" (undated).
Niculescu, et al. Efficacy of an adsorbed trivalent split influenza vaccine administered by intradermal route. Arch. Roum. Path. Exp. Microbiol. 1981, 40(1):67-70.
Nishimura et al., 1984, "Immunological activity of chitin and its derivatives," Vaccine 2:93-99.
Payler DK., Intradermal influenza vaccine using Portojet 1976. Br. Med. J. Oct. 29, 1977;2(6095):1152.
Payler, et al., Letter: Intradermal influenza vaccination. Br. Med. J. Jun. 29, 1974;2(921):727.
Peppas et al., 1996, "Hydrogels as mucoadhesive and bioadhesive materials: a review," Biomaterials 17(16):1553-1561.
Phillips et al., "Purified Influenza Vaccine: Clinical and Serologic Responses to Varying Doses and Different Routes of Immunization," Department of Medicine and Community Medicine, University of Vermont College of Medicine, Burlington, Vermont, J Infect Dis; Jul.-Aug. 1970;122(1):26-32.
Playford et al., "Intradermal recombinant hepatitis B vaccine for healthcare workers who fail to respond to intramuscular vaccine," Infect Control Hosp Epidemiol. Feb. 2002;23(2):87-90.
Polilio et al., "Does a Needleless Injection System Reduce Anxiety in Children Receiving Intramuscular Injections?," Pediatric Primary Care Clinic, Boston City Hospital, MA, USA.; Pediatr Nurs;. Jan.-Feb. 1997;23(1):46-9.
Propst et al., "Reinforced intradermal hepatitis B Vaccination," Am J Kidney Dis; Dec. 1998;32(6):1041-5.
Rahman et al., "Cellular and Humoral Immune Responses Induced by Intradermal or Intramuscular Vaccination with the major Hepatitis B Surface Antigen," Hepatology; Feb. 2000;31(2):521-7.
Renfrey et al., "Morphological and Biochemical Characterization of Influenza Vaccines Commercially Available in the United Kingdom," Vaccine; 1994;12(8).
Rindfleisch et al., "La Crosse finding could curtail flu vaccine shortages," *Wisconsin State Journal D9* (Nov. 14, 2004).
Robinson et al., 1987, "Bioadhesive polymers for controlled drug delivery," Ann NY Acad. Sci. 507:307-314.
Ropac et al., "Immunization against Hepatitis B: comparison of immune response to intradermal, intramuscular, and combined vaccination," Periodicum Bilogorium; 2001;103(1):39-43.
Ryan et al., "Immunomodulators and delivery systems for vaccination by mucosal routes," *Trends in Biotechnology* 19(8):293-304 (2001).
Scott, et al., Toxicity of Interferon, vol. 282, pp. 1345-1348, British Medical Journal, Apr. 25, 1981.
Seferian et al., "Immune stimulating activity of two new chitosan containing adjuvant formulations," *Vaccine* 19:661-668 (2001).
Shute, "Second thoughts on the flu vaccine," *Science & Society; Public Health* 137(17):80.
Singla et al., 2001, "Chitosan: Some pharmaceutical and biological aspects—an update," J. Pharmacy and Pharmacol. 53:1047-1067.
Smith, "Low-dose vaccine helps block flu, syudy says younger adults seen benefiting," *The Boston Globe: Nationla/Foreign* A2 (Nov. 4, 2004).
Smith Kline Beecham Meeting Agenda.
Steinman, "The Dendritic Cell System and Its Role in Immunogenicity," Annu Rev Immunol; 1991;9:271-96.
Supersaxo, et al., Recombinant Human Interferon Alpha-2a: Delivery to Lymphoid Tissue by Selected Modes of Application, Pharmaceutical Research, vol. 5, No. 8, pp. 472-476, Aug. 1998.
Sutherest, Treatment of Pruritus Vulvae by Multiple Intradermal Injections of Alcohol. A Double-Blind Study, vol. 86, pp. 371-373, British Journal of Obstetrics and Gynecology, May 1979.
Sveinsson, 1993, Investigation on the Influence of Insulin and Adrenalin in Rabbits with Alimentary Fatty Liver and Muscles and on the Content of Fat and Sugar in Blood, Oslo, Norway (pp. 66-86).
Takayama et al., 1991, "Adjuvant activity of non-ionic block copolymers. V. Modulation of antibody isotype by lipopolysaccharides, lipid A and precursors," Vaccine 9(4):257-265.
Tauraso et al. Effect of dosage and route of inoculation upon antigenicity of inactivated influenza virus vaccine (Hong Kong strain) in man. Bull. World Health Organ. 1969;41(3):507-16.
The American Heritage College Dictionary, 2000, 3rd Edition; Houghton Mifflin Company, Boston, New York, p. 368.
The Merck Manual of Diagnosis and Therapy, 1999, 17th Edition, Beers & Berkow, ed., Merck Research Laboratories, Division of Merck & Co., Inc., Whitehouse Station, NJ, pp. 2559-2567.
Todd et al., 1997, "Development of an adjuvant active nonionic block copolymer for use in oil-free subunit vaccines formulation," Vaccine 15:564-570.
Todd et al., 1998, "Systematic development of a block copolymer adjuvant for trivalent influenza virus vaccine," Dev. Biol. Stand. 92:341-351.

Van Der Lubben et al., "Chitosan and its derivatives in mucosal drug and vaccine delivery," *European Journal of Pharmaceutical Sciences* 14:201-207 (2001).

Van Der Lubben et al., "Chitosan for mucosal vaccination," *Advanced Drug Delivery Reviews* 52:139-144 (2001).

Verheul et al., 1992, "Nonionic block polymer surfactants as immunological adjuvants," Res. Immunol. 143(5):512-519, discussion pp. 574-576.

Vogel et al., 1995, "A compendium of vaccine adjuvants and excipients," in M.F. Powell, M.J. Newman (eds.) Plenum Press, New York pp. 141-228.

Von Hoegen, "Synthetic biomimetic supra molecular Biovector™ (SMBV™) particles for nasal vaccine delivery," *Advanced Drug Delivery Reviews* 51:113-125 (2001).

Ward, et al., Puritus Vulvae: Treatment by Multiple Intradermal Alcohol Injections, vol. 93, No. 2, pp. 201-204, British Journal of Dermatology, Aug. 1975.

Westerink et al., "ProJuvant™ (Pluronic F127®/chitosan) enhances the immune response to intranasally administered tetanus toxoid," *Vaccine* 20:711-723 (2002).

Whittle et al., "Trials of Intradermal Hepatitis B Vaccines in Gambian Children," Ann Trop Paediatr; Mar. 1987;7(1):6-9.

Woodley, 2001, "Bioadhesion: New possibilities for drug administration?" Clin. Pharmacokinet. 40(2):77-84.

Wu, et al., Pharmacokinetics of Methoxyflurane after its Intra-Dermal Injections as Lecithin-Coated Microdroplets, vol. 9, pp. 1-12, Journal of Controlled Release, Jul. 1989.

Zaynoun, et al., The Effect of Intracutaneous Glucocorticoids on Plasma Cortisol Levels, vol. 88, No. 2, pp. 151-156, British Journal of Dermatology, Feb. 1973.

Zigterman et al., 1987, "Adjuvant effects of nonionic block polymer surfactants on liposome-induced humoral immune response," J. Immunol. 138(1):220-225.

Degano P. et al., Intradermal DNA Immunization of Mice Against Influenza A Virus Using the Novel PowderJect System, Vaccine, vol. 16, No. 4, Feb. 1998 pp. 394-398.

Haensler J. et al., Intradermal DNA Immunization by Using Jet-Injectors in Mice and Monkeys, Vaccine, vol. 17, No. 7-8, Feb. 1999, pp. 628-638.

Raze. et al., Intrad. Gene Immun. the Possible Role of DNA Uptake in the Induction of Cell. Immunity to Viruses, Proc. Nat. Acad. Sci., vol. 91, No. 20, Sep. 1994 pp. 9519-23.

Heller R. et al., Intradermal Delivery of Interleukin-12 Plasmid DNA by in Vivo Electroporation, DNA and Cell Biology, vol. 20, No. 1, Jan. 2001 pp. 21-26.

Supplementary European Search Report for EP 02 76 3212, dated Oct. 14, 2005.

* cited by examiner

INTRADERMAL DELIVERY OF VACCINES AND GENE THERAPEUTIC AGENTS VIA MICROCANNULA

This application is a continuation-in-part of U.S. application Ser. No. 10/185,717, filed Jul. 1, 2002, now abandoned, which is herein incorporated by reference in its entirety.

1. BACKGROUND OF THE INVENTION

1.1 Field of the Invention

The present invention relates to methods and devices for administration of vaccines and gene therapeutic agents into the intradermal layer of skin.

1.2 Background Information

The importance of efficiently and safely administering pharmaceutical substances for the purpose of prophylaxis, diagnosis or treatment has long been recognized. The use of conventional needles has long provided one approach for delivering pharmaceutical substances to humans and animals by administration through the skin. Considerable effort has been made to achieve reproducible and efficacious delivery through the skin while improving the ease of injection and reducing patient apprehension and/or pain associated with conventional needles. Furthermore, certain delivery systems eliminate needles entirely, and rely upon chemical mediators or external driving forces such as iontophoretic currents or electroporation or thermal poration or sonophoresis to breach the stratum corneum, the outermost layer of the skin, and deliver substances through the surface of the skin. However, such delivery systems do not reproducibly breach the skin barriers or deliver the pharmaceutical substance to a given depth below the surface of the skin and consequently, clinical results can be variable. Thus, mechanical breach of the stratum corneum such as with needles, is believed to provide the most reproducible method of administration of substances through the surface of the skin, and to provide control and reliability in placement of administered substances.

Approaches for delivering substances beneath the surface of the skin have almost exclusively involved transdermal administration, i.e. delivery of substances through the skin to a site beneath the skin. Transdermal delivery includes subcutaneous, intramuscular or intravenous routes of administration of which, intramuscular (IM) and subcutaneous (SC) injections have been the most commonly used Anatomically, the outer surface of the body is made up of two major tissue layers, an outer epidermis and an underlying dermis, which together constitute the skin (for review, see *Physiology, Biochemistry, and Molecular Biology of the Skin, Second Edition*, L. A. Goldsmith, Ed., Oxford University Press, New York, 1991). The epidermis is subdivided into five layers or strata of a total thickness of between 75 and 150 µm. Beneath the epidermis lies the dermis, which contains two layers, an outermost portion referred to at the papillary dermis and a deeper layer referred to as the reticular dermis. The papillary dermis contains vast microcirculatory blood and lymphatic plexuses. In contrast, the reticular dermis is relatively acellular and avascular and made up of dense collagenous and elastic connective tissue. Beneath the epidermis and dermis is the subcutaneous tissue, also referred to as the hypodermis, which is composed of connective tissue and fatty tissue. Muscle tissue lies beneath the subcutaneous tissue.

As noted above, both the subcutaneous tissue and muscle tissue have been commonly used as sites for administration of pharmaceutical substances. The dermis, however, has rarely been targeted as a site for administration of substances, and this may be due, at least in part, to the difficulty of precise needle placement into the intradermal space. Furthermore, even though the dermis, in particular, the papillary dermis has been known to have a high degree of vascularity, it has not heretofore been appreciated that one could take advantage of this high degree of vascularity to obtain an improved absorption profile for administered substances compared to subcutaneous administration. This is because small drug molecules are typically rapidly absorbed after administration into the subcutaneous tissue that has been far more easily and predictably targeted than the dermis has been. On the other hand, large molecules such as proteins are typically not well absorbed through the capillary epithelium regardless of the degree of vascularity so that one would not have expected to achieve a significant absorption advantage over subcutaneous administration by the more difficult to achieve intradermal administration even for large molecules.

One approach to administration beneath the surface to the skin and into the region of the intradermal space has been routinely used in the Mantoux tuberculin test. In this procedure, a purified protein derivative is injected at a shallow angle to the skin surface using a 27 or 30 gauge needle and standard syringe (Flynn et al., *Chest* 106: 1463-5, 1994). The Mantoux technique involves inserting the needle into the skin laterally, then "snaking" the needle further into the ID tissue. The technique is known to be quite difficult to perform and requires specialized training. A degree of imprecision in placement of the injection results in a significant number of false negative test results. Moreover, the test involves a localized injection to elicit a response at the site of injection and the Mantoux approach has not led to the use of intradermal injection for systemic administration of substances. Another group reported on what was described as an intradermal drug delivery device (U.S. Pat. No. 5,997,501). Injection was indicated to be at a slow rate and the injection site was intended to be in some region below the epidermis, i.e., the interface between the epidermis and the dermis or the interior of the dermis or subcutaneous tissue. This reference, however, provided no teachings that would suggest a selective administration into the dermis nor did the reference suggest that vaccines or gene therapeutic agents might be delivered in this manner. To date, numerous therapeutic proteins and small molecular weight compounds have been delivered intradermally and used to effectively elicit a pharmacologically beneficial response. Most of these compounds (e.g., insulin, Neupogen, hGH, calcitonin) have been hormonal proteins not engineered receptors or antibodies. To date all administered proteins have exhibited several effects associated with ID administration, including more rapid onset of uptake and distribution (vs. SC) and in some case increased bioavailability.

Dermal tissue represents an attractive target site for delivery of vaccines and gene therapeutic agents. In the case of vaccines (both genetic and conventional), the skin is an attractive delivery site due to the high concentration of antigen presenting cells (APC) and APC precursors found within this tissue, in particular the epidermal Langerhan's cells and dermal dendritic cells. Several gene therapeutic agents are designed for the treatment of skin disorders, skin diseases and skin cancer. In such cases, direct delivery of the therapeutic agent to the affected skin tissue is desirable. In addition, skin cells are an attractive target for gene therapeutic agents, of which the encoded protein or proteins are active at sites distant from the skin. In such cases, skin cells (e.g., keratinocytes) can function as "bioreactors" producing a therapeutic protein that can be rapidly absorbed into the systemic circulation via the papillary dermis. In other cases, direct access of the vaccine or therapeutic agent to the systemic circulation is desirable for the treatment of disorders distant from the skin. In such cases, systemic distribution can be accomplished through the papillary dermis.

However, as discussed above, intradermal (ID) injection using standard needles and syringes is technically very difficult to perform and is painful. The prior art contains several references to ID delivery of both DNA-based and conventional vaccines and therapeutic agents, however results have been conflicting, at least in part due to difficulties in accurately targeting the ID tissue with existing techniques.

Virtually all of the human vaccines currently on the market are administered via the IM or SC routes. Of the 32 vaccines marketed by the 4 major global vaccine producers in the year 2001 (Aventis-Pasteur, GlaxoSmithKline, Merck, Wyeth), only 2 are approved for ID use (2001 *Physicians Desk Reference*). In fact, the product inserts for 6 of these 32 vaccines specifically states not to use the ID route. This is despite the various published pre-clinical and early clinical studies suggesting that ID delivery can improve vaccines by inducing a stronger immune response than via IM or SC injection or by inducing a comparable immune response at a reduced dose relative to that which is given IM or SC (Playford, E. G. et al., 2002, *Infect. Control Hosp. Epidemiol.* 23:87; Kerr, C. 2001, *Trends Microbiol.* 9:415; Rahman, F. et al., 2000, *Hepatology* 31:521; Carlsson, U. et al., 1996, *Scan J. Infect. Dis.* 28:435; Propst, T. et al., 1998, *Amer. J Kidney Dis.* 32:1041; Nagafuchi, S. et al., 1998, *Rev Med Virol.*, 8:97; Henderson, E. A., et al., 2000. *Infect. Control Hosp Epidemiol.* 21:264). Although improvements in vaccine efficacy following ID delivery have been noted in some cases, others have failed to observe such advantages (Crowe, 1965, *Am. J. Med. Tech.* 31:387-396; Letter to British Medical Journal 29/10/77, p. 1152; Brown et al., 1977, *J. Infect. Dis.* 136:466-471; Herbert & Larke, 1979, *J. Infect. Dis.* 140:234-238; Ropac et al. *Periodicum Biologorum* 2001, 103:39-43).

A major factor that has precluded the widespread use of the ID delivery route and has contributed to the conflicting results described above is the lack of suitable devices to accomplish reproducible delivery to the epidermal and dermal skin layers. Standard needles commonly used to inject vaccines are too large to accurately target these tissue layers when inserted into the skin. The most common method of delivery is through Mantoux-style injection using a standard needle and syringe. This technique is difficult to perform, unreliable and painful to the subject. Thus, there is a need for devices and methods that will enable efficient, accurate and reproducible delivery of vaccines and gene therapeutic agents to the intradermal layer of skin.

2. SUMMARY OF THE INVENTION

The present invention improves the clinical utility of ID delivery of vaccines and gene therapeutic agents to humans or animals. The methods employ devices to directly target the intradermal space and to deliver substances to the intradermal space as a bolus or by infusion. It has been discovered that the placement of the substance within the dermis provides for efficacious and/or improved responsiveness to vaccines and gene therapeutic agents. The device is so designed as to prevent leakage of the substance from the skin and improve adsorption or cellular uptake within the intradermal space. The immunological response to a vaccine delivered according to the methods of the invention has been found to be equivalent to or improved over conventional IM delivery of the vaccine, indicating that ID administration according to the methods of the invention will in many cases provide improved clinical results, in addition to the other advantages of ID delivery.

The present disclosure also relates to methods and devices for delivering vaccines or genetic material to an individual based on directly targeting the dermal space whereby such method allows improved delivery and/or an improved response to the vaccine or genetic material. By the use of direct intradermal (ID) administration means (hereafter referred to as dermal-access means), for example using microneedle-based injection and infusion systems, or other means to accurately target the intradermal space, the efficacy of many substances including vaccines and gene therapy agents can be improved when compared to traditional parental administration routes of subcutaneous and intramuscular delivery.

Accordingly, it is one object of the invention to provide a method to accurately target the ID tissue to deliver a vaccine or a medicament comprising genetic material to afford an immunogenic or therapeutic response.

It is a further object of the invention to provide a method to improve the systemic immunogenic or therapeutic response to vaccine (conventional or genetic) or medicament comprising genetic material by accurately targeting the ID tissue Yet another object of the invention is to provide a method to improve the availability of a vaccine (conventional or genetic) to APC residing in the skin in order to effectuate an antigen-specific immune response to the vaccine by accurately targeting the ID tissue. This may, in many cases, allow for smaller doses of the substance to be administered via the ID route.

Yet another object of the present invention is to provide a method to improve the delivery of a medicament comprising genetic material for the treatment of skin diseases, genetic skin disorders or skin cancer by accurately targeting the ID tissue. The resultant genetic material is subsequently expressed by the cells within the targeted ID tissue.

Yet another object of the present invention is to provide a method to improve the delivery of a medicament comprising genetic material for the treatment of diseases, genetic disorders, or cancers affecting tissues distant from the skin by accurately targeting the ID tissue. The resultant genetic material is subsequently expressed by the cells within the targeted ID tissue, distant therefrom or both.

These and other benefits of the invention are achieved by directly targeting delivery of the substance to the preferred depth for the particular therapeutic or prophylactic agent. The inventors have found that by specifically targeting delivery of the substance to the intradermal space, the response to vaccines and gene therapeutic agents can be unexpectedly improved, and can in many situations be varied with resulting clinical advantage.

3. BRIEF DESCRIPTION OF THE DRAWINGS

Figure 7:
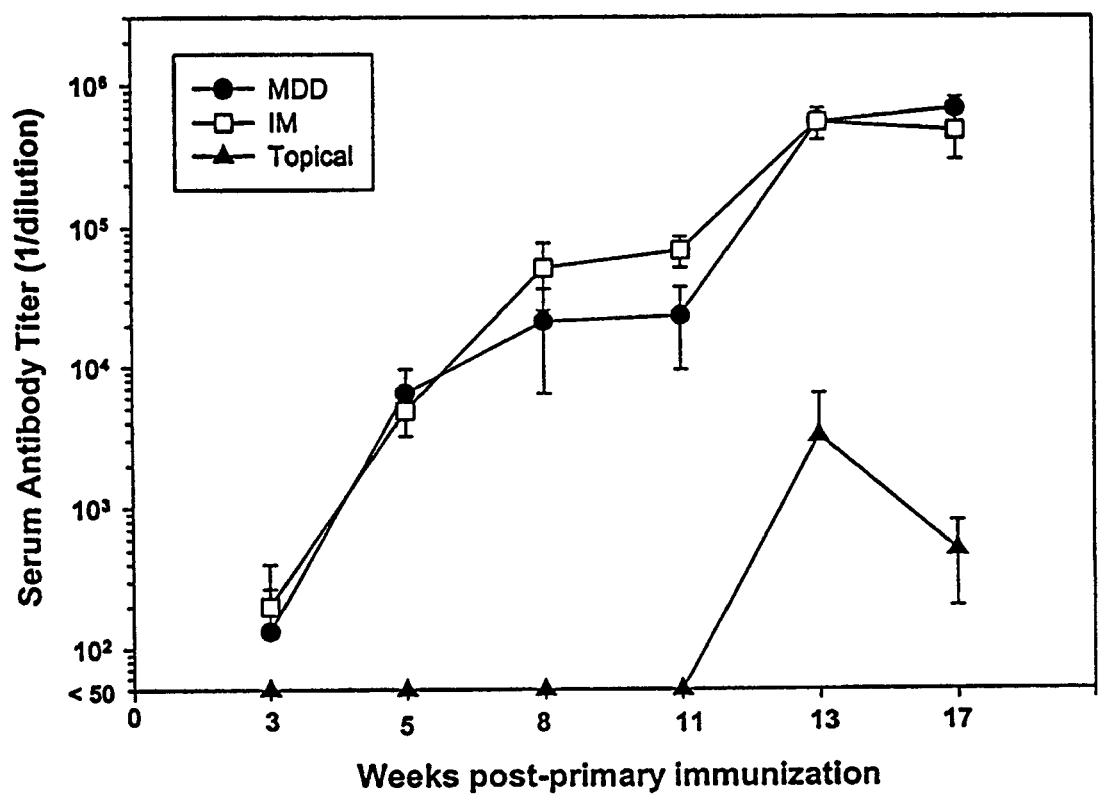

FIG. 7 shows the influenza-specific serum antibody response in rats following "priming" with plasmid DNA in the absence of added adjuvant followed by "boosting" with whole inactivated influenza virus in the absence of added adjuvant. Plasmid DNA or whole inactivated influenza virus was administered via ID delivery with the MDD device or via intramuscular (IM) injection with a standard needle and syringe. "Topical" indicates control group, where the preparation was topically applied to skin.

Figure 8:
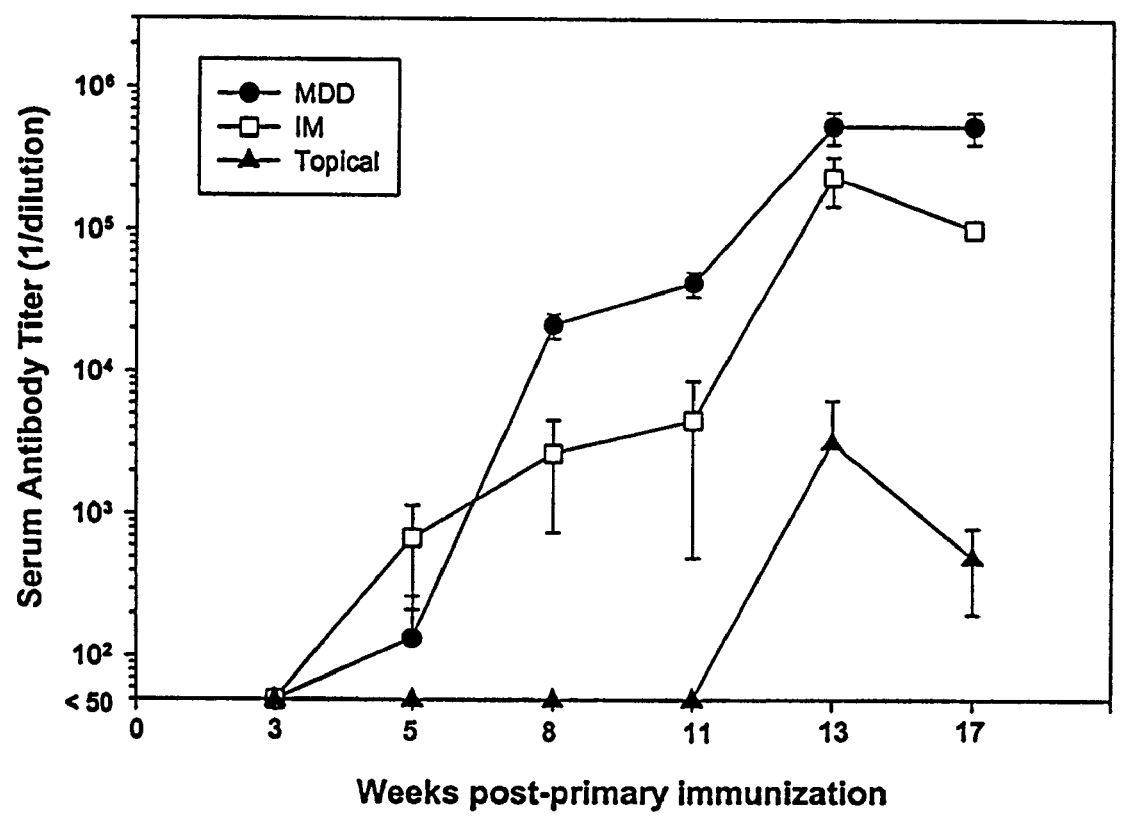

FIG. 8 shows the influenza-specific serum antibody response in rats following "priming" with plasmid DNA in the presence of added adjuvant followed by "boosting" with whole inactivated influenza virus in the absence of added adjuvant. Plasmid DNA or whole inactivated influenza virus was administered via ID delivery with the MDD device or via intra-muscular (IM) injection with a standard needle and syringe. "Topical" indicates control group, where the preparation was topically applied to skin.

Figure 9:
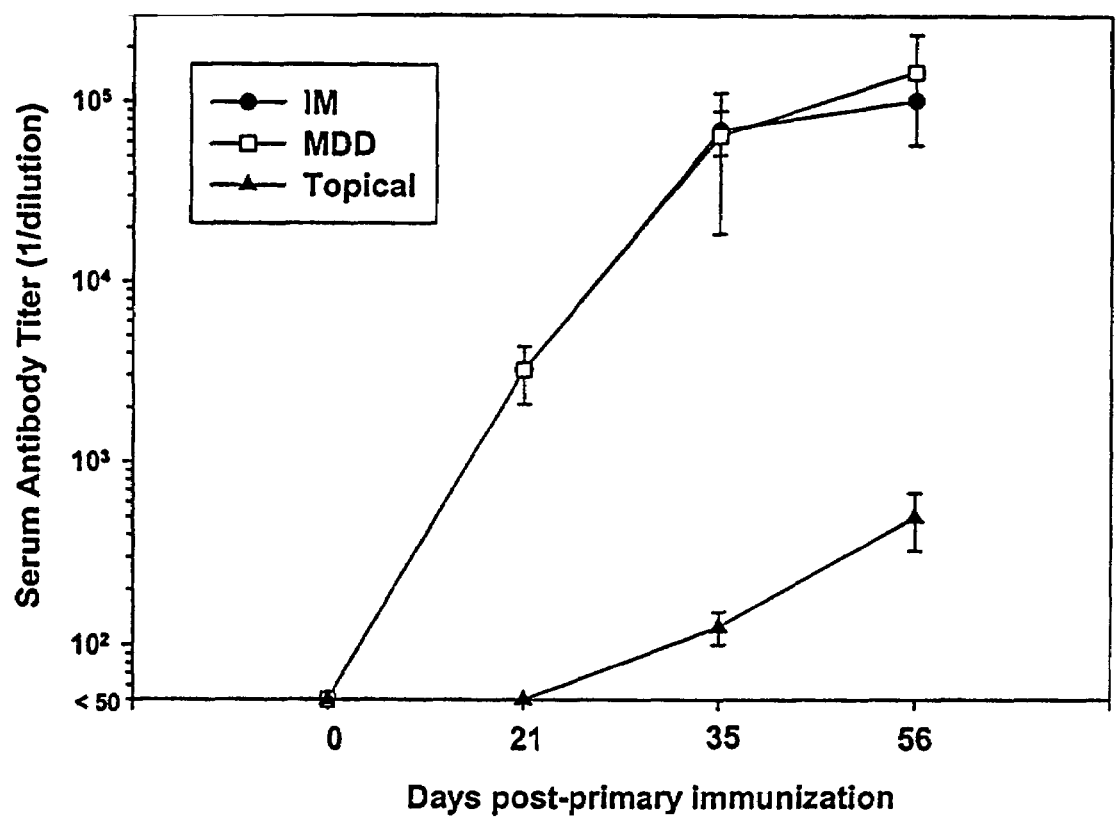

FIG. 9 shows the influenza-specific serum antibody response in rats to a whole inactivated influenza virus preparation administered via ID delivery with the MDD device or via intramuscular (IM) injection with a standard needle and syringe. "Topical" indicates control group, where the preparation was topically applied to skin.

Figure 10:
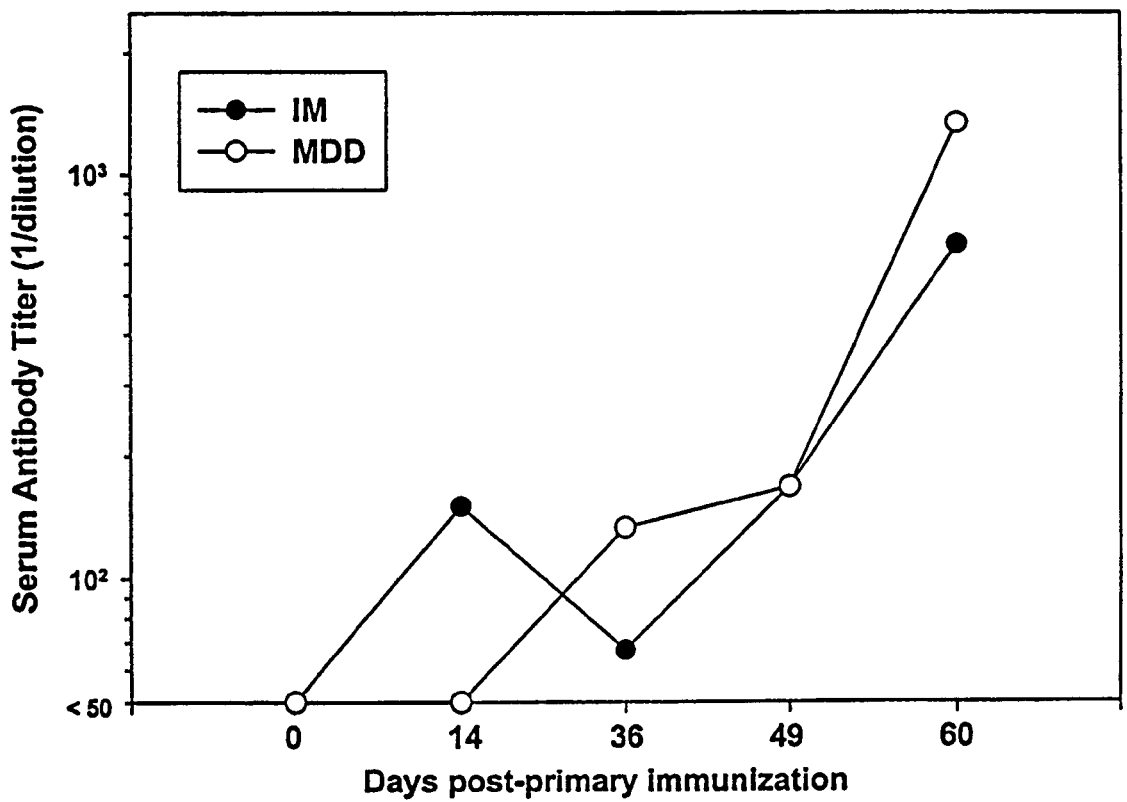

FIG. 10 shows the influenza-specific serum antibody response in pigs to a whole inactivated influenza virus preparation administered via ID delivery with the MDD device or via intramuscular (IM) injection with a standard needle and syringe.

Figure 11:
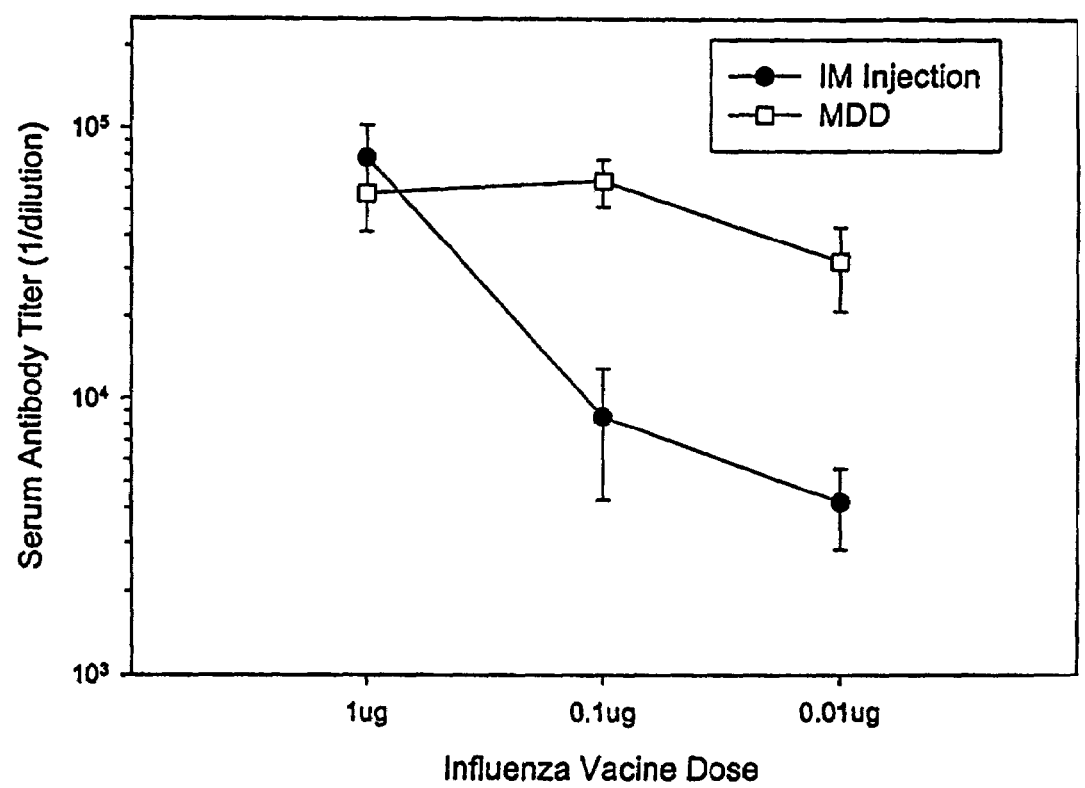

FIG. 11 shows the influenza-specific serum antibody response in rats to reduced doses of a whole inactivated influenza virus preparation administered via ID delivery with the MDD device or via IM injection with a standard needle and syringe.

4. DETAILED DESCRIPTION OF THE INVENTION

The present invention improves the clinical utility of ID delivery of vaccines and gene therapeutic agents to humans or animals. The methods encompass devices to directly target the intradermal space and to deliver substances to the intradermal space as a bolus or by infusion. It has been discovered that the placement of the substance within the dermis provides for efficacious and/or improved responsiveness to vaccines and gene therapeutic agents. The device is so designed as to prevent leakage of the substance from the skin and improve adsorption or cellular uptake within the intradermal space. The immunological response to a vaccine delivered according to the methods of the invention has been found to be equivalent to or improved over conventional IM delivery of the vaccine, indicating that ID administration according to the methods of the invention will in many cases provide improved clinical results, in addition to the other advantages of ID delivery.

As used herein, "intradermal" (ID) is intended to mean administration of a substance into the dermis in such a manner that the substance readily reaches the richly vascularized papillary dermis where it can be rapidly systemically absorbed, or in the case of vaccines (conventional and genetic) or gene therapeutic agents may be taken up directly by cells in the skin. In the case of genetic vaccines, intended target cells include APC (including epidermal Langerhan's cells and dermal dendritic cells). In the case of gene therapeutic agents for diseases, genetic disorders or cancers affecting tissues distant from the skin, intended target cells include keratinocytes or other skin cells capable of expressing a therapeutic protein. In the case of gene therapeutic agents for diseases, genetic disorders or cancers affecting the skin, the intended target cells include those skin cells which may be affected by the disease, genetic disorder or cancer.

As used herein, "targeted delivery" means delivery of the substance to the target depth, and includes delivery that may result in the same response in a treated individual, but result in less pain, more reproducibility, or other advantage compared to an alternate accepted means of delivery (e.g., topical, subcutaneous or intramuscular).

As used herein, an "improved response" includes an equivalent response to a reduced amount of compound administered or an increased response to an identical amount of compound that is administered by an alternate means of delivery or any other therapeutic or immunological benefit.

The terms "needle" and "needles" as used herein are intended to encompass all such needle-like structures. The terms microcannula or microneedles, as used herein, are intended to encompass structures smaller than about 31 gauge, typically about 31-50 gauge when such structures are cylindrical in nature. Non-cylindrical structures encompassed by the term microneedles would be of comparable diameter and include pyramidal, rectangular, octagonal, wedged, and other geometrical shapes.

As used herein, the term "bolus" is intended to mean an amount that is delivered within a time period of less than ten (10) minutes. A "rapid bolus" is intended to mean an amount that is delivered in less than one minute. "Infusion" is intended to mean the delivery of a substance over a time period greater than ten (10) minutes.

The term "nucleic acids" includes polynucleotides, RNA, DNA, or RNA/DNA hybrid sequences of more than one nucleotide in either single chain or duplex form, and may be of any size that can be formulated and delivered using the methods of the present invention, Nucleic acids may be of the "antisense" type. By "nucleic acid derived entity" is meant an entity composed of nucleic acids in whole or in part.

By "gene therapeutic agent" is meant an agent that is intended to be delivered into or be capable of uptake by cell(s) of the treated individual for incorporation and expression of genetic material. The gene therapeutic agent will ordinarily include a polynucleotide that encodes a peptide, polypeptide, protein or glycoprotein of interest, optionally contained in a vector or plasmid, operationally linked to any further nucleic acid sequences necessary for expression.

When referring to the administration of vaccines or gene therapeutic agents, the term "simultaneously" is generally means the administration of two dosages within the same 24 hour period, whereas "sequentially" or "subsequently" is intended to mean that the dosages are separated by more than 24 hours. It will be appreciated by those of skill in the art that simultaneous administration will generally refer to dosages administered at the same medical visit, whereas subsequently or sequentially will refer to dosages that may be separated by days, weeks, months, and occasionally years, depending on the effects of a particular vaccine or gene therapeutic. In one preferred embodiment, "sequential" or "subsequent" refers to dosages that are separated by one day to six weeks.

The desired therapeutic or immunogenic response is directly related to the ID targeting depth. These results can be obtained by placement of the substance in the upper region of the dermis, i.e., the papillary dermis or in the upper portion of the relatively less vascular reticular dermis such that the substance readily diffuses into the papillary dermis. Placement of a substance predominately at a depth of at least about 0.025 mm to about 2.5 mm is preferred.

4.1 Delivery and Administration of Vaccines and Gene Therapeutic Agents

The invention encompasses delivering a vaccine or gene therapeutic agents to the intradermal space of a subject's skin. In particular, for vaccines, it is preferred that delivery be at a targeted depth of just under the stratum corneum and encompassing the epidermis and upper dermis (about 0.025 mm to about 2.5 mm). For therapeutics that target cells in the skin, the preferred target depth depends on the particular cell being targeted; for example to target the Langerhans cells, delivery would need to encompass at least in part the epidermal tissue depth typically ranging from about 0.025 mm to about 0.2 mm in humans. For therapeutics and vaccines that require systemic circulation, the preferred target depth would be between, at least about 0.4 mm and most preferably at least about 0.5 mm up to a depth of no more than about 2.5 mm, more preferably, no more than about 2.0 mm and most preferably no more than about 1.7 mm will result delivery of the substance to the desired dermal layer. Placement of the substance predominately at greater depths and/or into the lower portion of the reticular dermis is usually considered to be less desirable.

The dermal-access means used for ID administration according to the invention is not critical as long as it provides the insertion depth into the skin of a subject necessary to provide the targeted delivery depth of the substance. In most cases, the device will penetrate the skin and to a depth of about 0.5-2 mm. The dermal-access means may comprise conventional injection needles, catheters, microcannula or microneedles of all known types, employed singularly or in multiple needle arrays.

By varying the targeted depth of delivery of substances by the dermal-access means, behavior of the drug or substance can be tailored to the desired clinical application most appropriate for a particular patient's condition. The targeted depth of delivery of substances by the dermal-access means may be controlled manually by the practitioner, or with or without the assistance of indicator means to indicate when the desired depth is reached. Preferably however, the device has structural means for controlling skin penetration to the desired depth within the intradermal space. This is most typically accomplished by means of a widened area or hub associated with the dermal-access means that may take the form of a backing structure or platform to which the needles are attached. The length of microneedles as dermal-access means are easily varied during the fabrication process and are routinely produced. Microneedles are also very sharp and of a very small gauge, to further reduce pain and other sensation during the injection or infusion. They may be used in the invention as individual single-lumen microneedles or multiple microneedles may be assembled or fabricated in linear arrays or two-dimensional arrays as to increase the rate of delivery or the amount of substance delivered in a given period of time. Microneedles having one or more sideports are also included as dermal access means. Microneedles may be incorporated into a variety of devices such as holders and housings that may also serve to limit the depth of penetration. The dermal-access means of the invention may also incorporate reservoirs to contain the substance prior to delivery or pumps or other means for delivering the drug or other substance under pressure. Alternatively, the device housing the dermal-access means may be linked externally to such additional components. The dermal-access means may also include safety features, either passive or active, to prevent or reduce accidental injury.

In one embodiment of the invention, ID injection can be reproducibly accomplished using one or more narrow gauge microcannula inserted perpendicular to the skin surface. This method of delivery ("microdermal delivery" or "MDD") is easier to accomplish than standard Mantoux-style injections and, by virtue of its limited and controlled depth of penetration into the skin, is less invasive and painful. Furthermore, similar or greater biological responses, as measured here by gene expression and immune response, can be attained using the MDD devices compared to standard needles. Optimal depth for administration of a given substance in a given species can be determined by those of skill in the art without undue experimentation.

Delivery devices that place the dermal-access means at an appropriate depth in the intradermal space, control the volume and rate of fluid delivery and provide accurate delivery of the substance to the desired location without leakage are most preferred. Micro-cannula- and microneedle-based methodology and devices are described in EP 1 092 444 A1, and U.S. application Ser. No. 606,909, filed Jun. 29, 2000. Standard steel cannula can also be used for intra-dermal delivery using devices and methods as described in U.S. Ser. No. 417,671, filed Oct. 14, 1999, the contents of each of which are expressly incorporated herein by reference. These methods and devices include the delivery of substances through narrow gauge (about 30 G) "micro-cannula" with limited depth of penetration, as defined by the total length of the cannula or the total length of the cannula that is exposed beyond a depth-limiting feature. These methods and devices provide for the delivery of substances through 30 or 31 gauge cannula, however, the present invention also employs 34 G or narrower "microcannula" including if desired, limited or controlled depth of penetration means. It is within the scope of the present invention that targeted delivery of substances can be achieved either through a single microcannula or an array of microcannula (or "microneedles"), for example 3-6 microneedles mounted on an injection device that may include or be attached to a reservoir in which the substance to be administered is contained.

Using the methods of the present invention, vaccines and gene therapeutic agents may be administered as a bolus, or by infusion. It is understood that bolus administration or delivery can be carried out with rate controlling means, for example a pump, or have no specific rate controlling means, for example, user self-injection. The above-mentioned benefits are best realized by accurate direct targeted delivery of substances to the dermal tissue compartment including the epidermal tissue. This is accomplished, for example, by using microneedle systems of less than about 250 micron outer diameter, and less than 2 mm exposed length. By "exposed length" it is meant the length of the narrow hollow cannula or needle available to penetrate the skin of the patient. Such systems can be constructed using known methods for various materials including steel, silicon, ceramic, and other metals, plastic, polymers, sugars, biological and or biodegradable materials, and/or combinations thereof.

It has been found that certain features of the intradermal administration methods provide the most efficacious results. For example, it has been found that placement of the needle outlet within the skin significantly affects the clinical response to delivery of a vaccine or gene therapy agent. The outlet of a conventional or standard gauge needle with a bevel angle cut to 15 degrees or less has a relatively large "exposed height". As used herein the term exposed height refers to the length of the opening relative to the axis of the cannula resulting from the bevel cut. When standard needles are placed at the desired depth within the intradermal space (at about 90 degrees to the skin), the large exposed height of these needle outlets causes the substance usually to effuse out of the skin due to backpressure exerted by the skin itself and to pressure built up from accumulating fluid from the injection or infusion. Typically, the exposed height of the needle outlet of the present invention is from 0 to about 1 mm. A needle outlet with an exposed height of 0 mm has no bevel cut (or a bevel angle of 90 degrees) and is at the tip of the needle. In this case, the depth of the outlet is the same as the depth of penetration of the needle. A needle outlet that is either formed by a bevel cut or by an opening through the side of the needle has a measurable exposed height. In a needle having a bevel, the exposed height of the needle outlet is determined by the diameter of the needle and the angle of the primary bevel cut ("bevel angle"). In general, bevel angles of greater than 20° are preferred, more preferably between 25° and 40°. It is understood that a single needle may have more than one opening or outlet suitable for delivery of substances to the dermal space.

Thus the exposed height, and for the case of a cannula with an opening through the side, its position along the axis of the cannula contributes to the depth and specificity at which a substance is delivered. Additional factors taken alone or in combination with the cannula, such as delivery rate and total fluid volume delivered, contribute to the target delivery of substances and variation of such parameters to optimize results is within the scope of the present invention.

It has also been found that controlling the pressure of injection or infusion may avoid the high backpressure exerted during ID administration. By placing a constant pressure directly on the liquid interface a more constant delivery rate can be achieved, which may optimize absorption and obtain an improved response for the dosage of vaccine or therapeutic agent delivered. Delivery rate and volume can also be controlled to prevent the formation of wheals at the site of delivery and to prevent backpressure from pushing the dermal-access means out of the skin. The appropriate delivery rates and volumes to obtain these effects for a selected substance may be determined experimentally using only ordinary skill and without undue experimentation. Increased spacing between multiple needles allows broader fluid distribution and increased rates of delivery or larger fluid volumes.

In one embodiment, to deliver a substance the dermal-access means is placed adjacent to the skin of a subject providing directly targeted access within the intradermal space and the substance or substances are delivered or administered into the intradermal space where they can act locally or be absorbed by the bloodstream and be distributed systemically. In another embodiment, the dermal-access means is positioned substantially perpendicular to the skin surface to provide vertical insertion of one or more cannula. The dermal-access means may be connected to a reservoir containing the substance or substances to be delivered. The form of the substance or substances to be delivered or administered include solutions thereof in pharmaceutically acceptable diluents or solvents, emulsions, suspensions, gels, particulates such as micro- and nanoparticles either suspended or dispersed, as well as in-situ forming vehicles of the same. Delivery from the reservoir into the intradermal space may occur either passively, without application of the external pressure or other driving means to the substance or substances to be delivered, and/or actively, with the application of pressure or other driving means. Examples of preferred pressure generating means include pumps, syringes, elastomer membranes, gas pressure, piezoelectric, electromotive, electromagnetic pumping, coil springs, or Belleville springs or washers or combinations thereof. If desired, the rate of delivery of the substance may be variably controlled by the pressure-generating means. As a result, the substance enters the intradermal space and is absorbed in an amount and at a rate sufficient to produce a clinically efficacious result.

4.2 Vaccines and Gene Therapeutic Agents

Substances that may be delivered according to the methods of the invention include vaccines, with or without carriers, adjuvants and vehicles, including prophylactic and therapeutic antigens including but not limited to subunit proteins, peptides and polysaccharides, polysaccharide conjugates, toxoids, genetic based vaccines, live attenuated bacteria or viruses, mutated bacteria or viruses, reassortant bacteria or viruses, inactivated bacteria or viruses, whole cells or components thereof (e.g., mammalian cells), cellular vaccines (e.g., autologous dendritic cells), or components thereof (for example, exosomes, dexosomes, membrane fragments, or vesicles), live viruses, live bacteria, viral and bacterial vectors including but not limited to those derived from adenoviruses, retroviruses alphaviruses, flaviviruses, and vaccinia viruses) in connection with addiction (e.g., cocaine addiction), anthrax, arthritis, cholera, diphtheria, dengue, tetanus, lupus, multiple sclerosis, parasitic diseases, psoriasis, Lyme disease, meningococcus, measles, mumps, rubella, varicella, yellow fever, Respiratory syncytial virus, tick borne Japanese encephalitis, pneumococcus, smallpox, streptococcus, staphylococcus, typhoid, influenza, hepatitis, including hepatitis A, B, C and E, otitis media, rabies, polio, HIV, parainfluenza, rotavirus, Epstein Barr Virus, CMV, chlamydia, nontypeable haemophilus, haemophilus influenza B (HIB), moraxella catarrhalis, human papilloma virus, tuberculosis including BCG, gonorrhoeae, asthma, atherosclerosis, malaria, *E. coli*, Alzheimer's Disease, *H. Pylori*, salmonella, diabetes, cancer, herpes simplex, human papilloma, *Yersinia pestis*, traveler's diseases, West Nile encephalitis, Camplobacter, *C. difficile*.

The vaccines used in the methods and compositions of the invention comprise one or more antigenic or immunogenic agent, against which an immune response is desired. In certain embodiments, the vaccine formulations of the invention comprise recombinant or chimeric viruses encoded by viral vectors derived from the genome of a virus, such as those listed supra. In accordance with the invention a recombinant virus is encoded by endogenous or native genomic sequences and/or non-native genomic sequences of a virus. A native or genomic sequence is one that is different from the native or endogenous genomic sequence due to one or more mutations, including, but not limited to, point mutations, rearrangements, insertions, deletions etc., to the genomic sequence that may or may not result in a phenotypic change. The recombinant viruses of the invention encompass those viruses encoded by viral vectors derived from the genomes of a virus, such as those listed supra, and may or may not, include nucleic acids that are non-native to the viral genome. In accordance with the invention, a chimeric virus may be encoded by a nucleotide sequence in which heterologous nucleotide sequences have been added to the genome or in which endogenous or native nucleotide sequences have been replaced with heterologous nucleotide sequences.

In certain embodiments, completely foreign epitopes, including antigens derived from other viral or non-viral pathogens can be engineered into the virus for use in the vaccine formulations of the invention. For example, antigens of viruses such as HIV (e.g., gp160, gp120, gp41, influenza, hepatitis, including hepatitis A, B, C and E, rabies, polio, HIV, parainfluenza, rotavirus, Epstein Barr Virus, CMV, flaviviruses including but not limited to, Japanese Encephalitis (JE, e.g., JE SA14-142), Dengue (DEN, e.g., any of the Dengue serotypes 1-4); Murray Valley encephalitis, St Louis Encephalitis, West Nile, Tick borne encephalitis, Hepatitis C viruses, Kunjin virus, Powassan virus, Kyasanur Forest Disease virus, and Omsk Hemorrhagic Fever Virus, parasite antigens (e.g., malaria), bacterial or fungal antigens or tumor antigens can be engineered into the attenuated strain.

Virtually any heterologous gene sequence may be constructed into the chimeric viruses of the invention for use in the vaccine formulations. Preferably, heterologous gene sequences are moieties and peptides that act as biological response modifiers. Preferably, epitopes that induce a protective immune response to any of a variety of pathogens, or antigens that bind neutralizing antibodies may be expressed by or as part of the chimeric viruses. For example, heterologous gene sequences that can be constructed into the chimeric viruses of the invention include, but are not limited to, influenza and parainfluenza hemagglutinin neuraminidase and fusion glycoproteins such as the HN and F genes of human PIV3. In yet another embodiment, heterologous gene sequences that can be engineered into the chimeric viruses include those that encode proteins with immuno-modulating activities. Examples of immuno-modulating proteins include, but are not limited to, cytokines, interferon type 1, gamma interferon, colony stimulating factors, interleukin-1, -2, -4, -5, -6, -12, and antagonists of these agents.

Other heterologous sequences may be derived from tumor antigens, and the resulting chimeric viruses be used to generate an immune response against the tumor cells leading to tumor regression in vivo. In accordance with the present invention, recombinant viruses may be engineered to express tumor-associated antigens (TAAs), including but not limited to, human tumor antigens recognized by T cells (Robbins and Kawakami, 1996, Curr. Opin. Immunol. 8:628-636, incorporated herein by reference in its entirety), melanocyte lineage proteins, including gp100, MART-1/MelanA, TRP-1 (gp75), tyrosinase; Tumor-specific widely shared antigens, MAGE-1, MAGE-3, BAGE, GAGE-1, GAGE-1, N-acetylglucosaminyltransferase-V, p15; Tumor-specific mutated antigens, β-catenin, MUM-1, CDK4; Nonmelanoma antigens for breast, ovarian, cervical and pancreatic carcinoma, HER-2/neu, human papillomavirus-E6, -E7, MUC-1.

In a preferred specific embodiment, the chimeric vaccines of the invention comprise recombinant chimeric flaviviruses encoded by viral vectors derived from genomes of yellow fever virus and one or more other flaviviruses. In a specific embodiment, the chimeric flaviviruses for use in the methods and compositions of the invention are preferably live, infectious, attenuated virus, comprising: (1) a first flavivirus, preferably a yellow fever virus, e.g., strain 17D, which is preferably a live attenuated vaccine virus, in which the nucleotide sequence encoding an envelope protein, e.g., the prM and E protein, is modified, for example by deletion, truncation or mutation so that the functional envelope protein of the first flavivirus is not expressed; (2) a nucleotide sequence encoding the viral envelope protein of a second flavivirus, i.e., Dengue virus, which is different from the first flavivirus, so that the envelope protein of the second flavivirus is expressed. The invention encompasses chimeric flavivirus vaccines known in the art, such as those disclosed in International Publication No. WO 01/39802, which is incorporated herein by reference in its entirety. In a preferred embodiment, the prM and E protein nucleotide encoding sequence of YF is replaced with the prM and E protein nucleotide encoding sequence of a second flavivirus.

A preferred live virus for use as the first yellow fever in the chimeric vaccines of the invention is YF 17D, see, e.g,. Smithburn et al., Yellow Fever Vaccination, World Health Org. p. 238, 1956; Freestone, in Plotkin et al., eds, Vaccines, $2^{nd}$ ed, W. B, Saunders, Pa., 1995). YF has been studied at the genetic level (Rice et al. 1985, Science 229, 726-33). Other YF strains that may be used in the chimeric vaccine formulations of the invention include but are not limited to, YF 17DD (Genbank Accession No. U17066); YF-17D213 (Genbank Accession No. U17067), YF 17D-204 France (Genbank Accession No. X15067, X15062), and YF 17D-204, 234 US (Rice et al., 1985, Science 229, 726-33; Rice et al., New Biologist, 1: 285-96; Genbank Accession No. CO3700; K 02749). Other Yellow fever strains encompassed within the invention are described by Gallery et al., 1998, Vaccine, 16: 1024-28, which is incorporated herein by reference in its entirety.

Preferred flaviviruses for use as the second flavivirus in the chimeric viruses of the invention, include but are not limited to Japanese Encephalitis (JE, e.g., JE SA14-14-2), Dengue (DEN, e.g., any of the Dengue serotypes 1-4); Murray Valley encephalitis (MVE), St Louis Encephalitis (SLE), West Nile (WN), Tick borne encephalitis (TBE), Hepatitis C viruses, Kunjin virus, Powassan virus, Kyasanur Forest Disease virus, and Omsk Hemorrhagic Fever Virus.

In some embodiments, the second flavivirus envelope protein nucleotide encoding sequence in the chimeric flavivirus vaccines is derived from two different second flaviviruses, e.g., two Dengue strains. In some embodiments, the second flavivirus envelope protein nucleotide encoding sequence in the chimeric flavivirus vaccines is attenuated using methods known to one skilled in the art. When the second flavivirus is a neurotropic virus, such as Japanese Encephalitis, Murray Valley encephalitis (MVE), St Louis Encephalitis (SLE), the envelope protein nucleotide encoding sequence is preferably attenuated. In the case of non-neurotropic viruses, e.g., dengue virus, it may be preferable to use envelope protein nucleotide encoding sequences that are not attenuated. Although not intending to be bound by a particular mechanism of action, maintenance of native sequences may lead to enhanced immunogenicity, and thus a more effective vaccine.

In a preferred embodiment, the second flavivirus envelope protein nucleotide encoding sequence in the chimeric flavivirus vaccines is derived from two different second flaviviruses, e.g., two different Dengue strains. In some embodiments, the second flavivirus envelope protein nucleotide encoding sequence in the chimeric flavivirus vaccines is attenuated using methods known to one skilled in the art. In the case of non-neurotropic viruses, e.g. dengue virus, it may be preferable to use envelope protein nucleotide encoding sequences that are not attenuated. Although not intending to be bound by a particular mechanism of action, maintenance of native sequences may lead to enhanced immunogenicity, and thus a more effective vaccine.

The chimeric flavivirus vaccines of the invention are constructed using common recombinant DNA methodologies known to one skilled in the art. Preferably, the chimeric flavivirus vaccines of the invention are constructed in accordance with methods described in International Publication No. WO 01/39802, which is incorporated herein by reference in its entirety. In particular, the chimeric flavivirus vaccines of the invention are constructed using the principles set forth in International Publication No. WO 01/39802, ensuring proper proteolytic processing of the polypeptide. YF viral proteins are produced by translation of a single long open reading frame to generate a polyprotein. A complex series of posttranslational proteolytic processing coupled with host and viral proteases generate the mature viral proteins. The structural proteins are arranged in the order C-prM-E, where C is cased, prM is a precursor of the viral envelope bound M protein, and E is the envelope protein. A stretch of about 20 amino acids separates C-prM and is referred to as the prM signal sequence which is bound by the two proteolytic sites resulting in the release of the C and prM proteins. The amino terminus of prM is generated by host signalase cleavage within the lumen of the ER, and the NS2B-NS3 protease complex is responsible for mediating cleavage at the C terminus of the C protein. Maintenance of a coordinated cleavage of NS2B-NS3 protease complex at the C-terminus of the C protein and the signalase at the N terminus of the prM protein is critical for proper processing of the polyprotein. In particular, in the chimeric vaccines of the invention the length of the prM signal sequence separating the two cleavage sites is substantially maintained to ensure proper processing and subsequent viability of the chimeric viruses. In most preferred embodiments, in constructing the chimeric flavivirus of the invention the prM signal of the YF backbone is maintained. Preferably, when a sequence from the second flavivirus is introduced into the YF backbone, it is inserted after prM signal sequence. Preferably, the length and sequence of the YF prM signal is maintained. In some embodiments, the YF prM signal sequence may be modified by conservative amino acid substitutions.

The invention encompasses vaccine formulations in which the virus is attenuated. Production of recombinant, chimeric and attenuated viruses may be performed using standard methods known to one skilled in the art. The invention encompasses a live recombinant viral vaccine or an inactivated recombinant viral vaccine to be formulated in accordance with the invention. A live vaccine may be preferred because multiplication in the host leads to a prolonged stimulus of similar kind and magnitude to that occurring in natural infections, and therefore, confers substantial, long-lasting immunity. Production of such live recombinant virus vaccine formulations may be accomplished using conventional methods involving propagation of the virus in cell culture or in the allantois of the chick embryo followed by purification.

In a specific embodiment, the recombinant virus used in the vaccine formulations of the invention is non-pathogenic to the subject to which it is administered. In this regard, the use of genetically engineered viruses for vaccine purposes may require the presence of attenuation characteristics in these strains. The introduction of appropriate mutations (e.g., deletions) into the templates used for transfection may provide the novel viruses with attenuation characteristics. For example, specific missense mutations which are associated with temperature sensitivity or cold adaption can be made into deletion mutations. These mutations should be more stable than the point mutations associated with cold or temperature sensitive mutants and reversion frequencies should be extremely low.

Alternatively, chimeric viruses with "suicide" characteristics may be constructed for use in the vaccine formulations of the invention. Such viruses would go through only one or a few rounds of replication within the host. When used as a vaccine, the recombinant virus would go through limited replication cycle(s) and induce a sufficient level of immune response but it would not go further in the human host and cause disease.

Alternatively, inactivated (killed) virus may be formulated in accordance with the invention. Inactivated vaccine formulations may be prepared using conventional techniques to "kill" the chimeric viruses. Inactivated vaccines are "dead" in the sense that their infectivity has been destroyed. Ideally, the infectivity of the virus is destroyed without affecting its immunogenicity. In order to prepare inactivated vaccines, the chimeric virus may be grown in cell culture or in the allantois of the chick embryo, purified by zonal ultracentrifugation, inactivated by formaldehyde or β-propiolactone, and pooled.

Suitable exemplary compositions for genetic immunization are described, for example, in U.S. Pat. Nos. 5,589,466, 5,593,972 and 5,703,055, all of which are incorporated herein by reference in their entireties.

Particularly preferred substances that can be delivered according to the methods of the invention include nucleic acids, nucleic acid derived entities and gene therapeutic agents and the like used in the prevention, diagnosis, alleviation, treatment, or cure of disease. Suitable adjuvants for inclusion in vaccines are known to those of skill in the art. Additional agents for enhancing immune response that may be used in the present invention are disclosed in U.S. application Ser. No. 10/142,966, filed May 13, 2002, which is incorporated herein by reference in its entirety.

Particularly preferred gene therapeutic agents include those indicated for the treatment of cancer including but not limited to melanoma, cutaneous T cell lymphoma, Kaposi's sarcoma, cutaneous squamous cell carcinoma and basal cell carcinoma, adenosine deaminase deficiency, hyperproliferative skin diseases including but not limited to psoriasis, genetic skin diseases including but not limited to epidermolytic hyperkeratosis, epidermolysis bullosa, lamellar ichthyosis and X-linked ichthyosis, hemophilia, cystic fibrosis, growth disorders, hormone deficiencies including but not limited to human growth hormone deficiency, atherosclerosis, transferrin deficiency, as well as gene therapeutic agents indicated for wound healing and tissue regeneration. Suitable exemplary compositions for suitable genetic therapeutic agents are described, for example, in U.S. Pat. No. 5,547,932, which is incorporated herein by reference in its entirety.

The substance may be delivered into the skin in any pharmaceutically acceptable form. Vaccines to be used in the methods of the invention may include adjuvants and carriers or vehicles that are suitable in particular formulations, as will be familiar to those of skill in the art.

Pharmaceutically acceptable peptide and polypeptide formulations for use in the invention, including formulations for allergen compositions, are also well known in the art. Nucleic acids for use in the methods of the invention may be RNA or DNA, or a combination thereof. They may be in any physical form suitable for ID administration and for uptake and expression by cells. DNA and/or RNA may be contained in a viral vector or liposome, or may be delivered as a free polynucleotide such as a plasmid as is known in the art. The nucleic acid will typically be formulated in a pharmaceutically acceptable formulation such as a fluid, gel, or suspension that is compatible with the nucleic acid.

5. Kits

Typically, to administer vaccine or other medicament a practitioner will remove the appropriate volume from a vial sealed with a septa using a syringe. This same syringe is then used administer the vaccine to the patient. However, a microneedle or microcannula, typically between 0.1 and 2 mm in length, in addition to being somewhat unsuitable in length to completely penetrate the septa, is generally too fragile to puncture a septum of a vial to extract medicament while maintaining sufficient sharpness and straightness to subsequently be used on a patient. Use of such microdevices in puncturing septa also may result in clogging of the bore of the needle. In addition, the narrow gauge, typically 31 to 50 gauge, of the microcannula greatly reduces the volumetric capacity that can traverse the needle into the syringe, for example. This would be inconvenient to most practitioners who are accustomed to rapid transfer of liquids from vials using conventional devices and thus would greatly increase the amount of time the practitioner would spend with the patient. Additional factors to be considered in the widespread use of microdevices include the necessity to reformulate most drugs and vaccines to accommodate the reduced total volume (10-100 µl) used or delivered by microdevices. Thus it would be desirable to provide for a kit including the device either in combination with or adapted to integrate therewith, the substance to be delivered.

Kits and the like comprising the instrument of administration and the therapeutic composition are well known in the art. However, the application of minimally invasive, ID microdevices for the delivery of drugs and vaccines clearly present an immediate need for coupling the device with the formulation to provide safe, efficacious, and consistent means for administering formulations for enabling immunogenic and therapeutic responses.

The kit provided by the invention comprises a delivery device having at least one hollow microneedle designed to intradermally deliver a substance to a depth between 0.025 and 2 mm which is adapted so that the microneedle is or can be placed in fluid connection with a reservoir adapted for containing a dosage of a vaccine or gene therapeutic. In a preferred embodiment, the kit also contains an effective dosage of a vaccine or gene therapeutic, optionally contained in a reservoir that is an integral part of, or is capable of being functionally attached to, the delivery device. The hollow microneedle is preferably between about 31 to 50 gauge, and may be part of an array of, for example, 3-6 microneedles.

In a particularly preferred embodiment, the kit of the invention comprises a hub portion being attachable to the prefillable reservoir storing the vaccine; at least one microneedle supported by said hub portion and having a forward tip extending away from said hub portion; and a limiter portion surrounding said microneedle(s) and extending away from said hub portion toward said forward tip of said microneedle(s), said limiter including a generally flat skin engaging surface extending in a plane generally perpendicular to an axis of said microneedle(s) and adapted to be received against the skin of a mammal to administer an intradermal injection of the vaccine, said microneedle(s) forward tip(s) extending beyond said skin engaging surface a distance approximately 0.5 mm to 2.0 mm wherein said limiter portion limits penetration of the microneedle(s) into the dermal layer of skin of the mammal.

To use a kit as envisioned by the instant invention the practitioner would break a hermetic seal to provide access to the microdevice and optionally, the vaccine or immunogenic or therapeutic composition. The composition may be pre-loaded within the microdevice in any form including but not limited to gel, paste, oil, emulsion, particle, nanoparticle, microparticle, suspension or liquid. The composition may be separately packaged within the kit package, for example, in a reservoir, vial, tube, blister, pouch or the like. One or more of the constituents of the formulation may be lyophilized, freeze-dried, spray freeze-dried, or in any other reconstitutable form. Various reconstitution media, cleansing or disinfective agents, or topical steriliants (alcohol wipes, iodine) can further be provided if desired. The practitioner would then load or integrate the substance if necessary into the device and then administer the formulation to the patient using the ID injection microdevice.

In a specific embodiment, the invention comprises kits comprising a device for intradermal delivery and a chimeric flavivirus vaccine formulation of the invention as described herein. In another specific embodiment, the invention provides a kit for use in inducing an immune response to a flavivirus viral antigen in a subject, said kit comprising: (a) a chimeric yellow fever virus expressing an envelope gene product of a flavivirus e.g., Dengue, J E and (b) a device that that targets the intradermal compartment of the subject's skin.

6. EXAMPLES

Having described the invention in general, the following specific but not limiting examples and reference to the accompanying Figures set forth various examples for practicing the invention.

A representative example of dermal-access microdevice (MDD device) comprising a single needle were prepared from 34 gauge steel stock (MicroGroup, Inc., Medway, Mass.) and a single 28° bevel was ground using an 800 grit carborundum grinding wheel. Needles were cleaned by sequential sonication in acetone and distilled water, and flow-checked with distilled water. Microneedles were secured into small gauge catheter tubing (Maersk Medical) using UV-cured epoxy resin. Needle length was set using a mechanical indexing plate, with the hub of the catheter tubing acting as a depth-limiting control and was confirmed by optical microscopy. The exposed needle length was adjusted to 1 mm using an indexing plate. Connection to the syringe was via an integral Luer adapter at the catheter inlet. During injection, needles were inserted perpendicular to the skin surface, and were held in place by gentle hand pressure for bolus delivery. Devices were checked for function and fluid flow both immediately prior to and post injection. A 30/31 gauge intradermal needle device with 1.5 mm exposed length controlled by a depth limiting hub as described in EP 1 092 444 A1 was also used in some Examples.

Example 1

ID Delivery and Expression of Model Genetic Therapeutic/Prophylactic Agents, Guinea Pig Model Uptake and expression of DNA by cells in vivo are critical to effective gene therapy and genetic immunization. Plasmid DNA encoding the reporter gene, firefly luciferase, was used as a model gene therapeutic agent (Aldevron, Fargo, N. Dak.). DNA was administered to Hartley guinea pigs (Charles River, Raleigh, N.C.) intradermally (ID) via the Mantoux (ID-Mantoux) technique using a standard 30 G needle or was delivered ID via MDD (ID-MDD) using a 34 G steel micro-cannula of 1 mm length (MDD device) inserted approximately perpendicular. Plasmid DNA was applied topically to shaved skin as a negative control (the size of the plasmid is too large to allow for passive uptake into the skin). Total dose was 100 μg per animal in total volume of 40 μl PBS delivered as a rapid bolus injection (<1 min) using a 1 cc syringe. Full thickness skin biopsies of the administration sites were collected 24 hr. following delivery, were homogenized and further processed for luciferase activity using a commercial assay (Promega, Madison, Wis.). Luciferase activity was normalized for total protein content in the tissue specimens as determined by BCA assay (Pierce, Rockford, Ill.) and is expressed as Relative Light Units (RLU) per mg of total protein (n=3 animals per group for Mantoux and Negative control and n=6 for MDD device).

Figure 1:
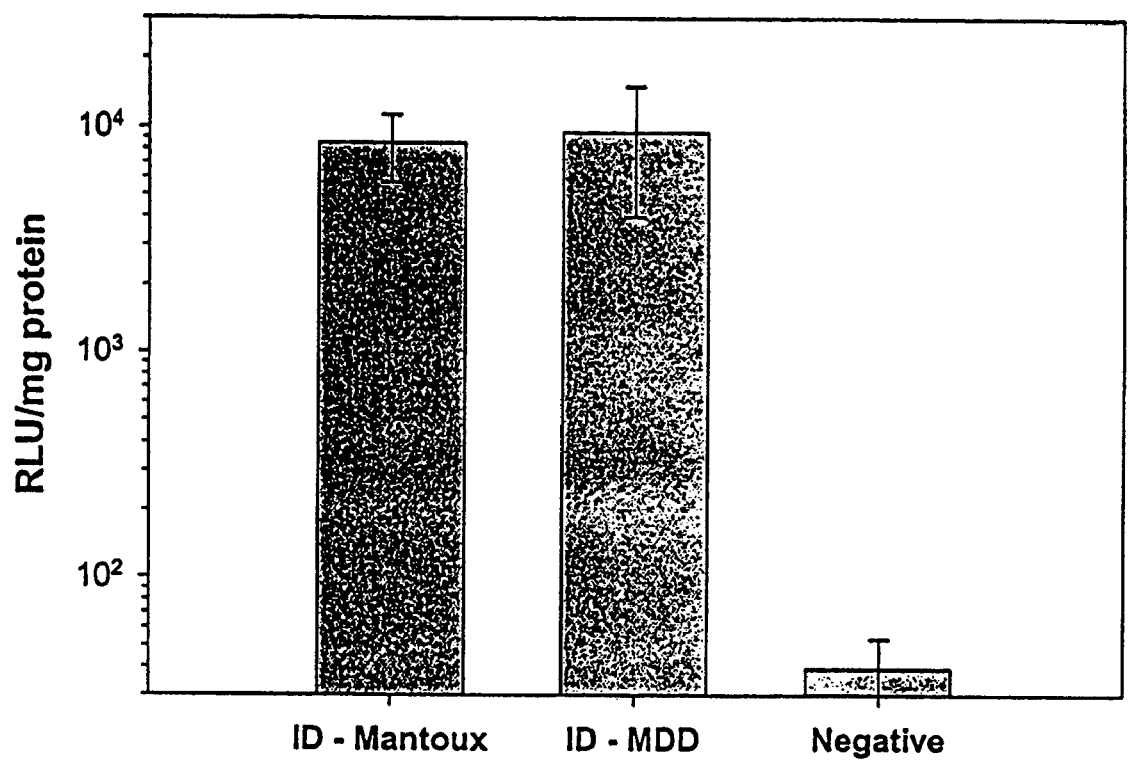
FIG. 1 shows reporter gene activity in guinea pig skin following delivery of plasmid DNA encoding firefly luciferase. Results are shown as relative light units (RLU) per mg protein for intradermal delivery by the Mantoux method, the delivery method of the invention, and control group in which topical application of the Plasmid DNA was made to shaved skin.

The results (FIG. 1) demonstrate strong luciferase expression in both ID injection groups. Mean luciferase activity in the MDD and Mantoux groups were 240- and 220-times above negative controls, respectively. Luciferase expression levels in topical controls were not significantly greater than in untreated skin sites (data not shown). These results demonstrate that the method of the present invention using MDD devices is at least as effective as the Mantoux technique in delivering genetic materials to the ID tissue and results in significant levels of localized gene expression by skin cells in vivo.

Example 2

ID Delivery and Expression of Model Genetic Therapeutic/Prophylactic Agents, Rat Model Experiments similar (without Mantoux control) to those described in Example 1 above were performed in Brown-Norway rats (Charles River, Raleigh, N.C.) to evaluate the utility of this platform across multiple species. The same protocol was used as in Example 1, except that the total plasmid DNA load was reduced to 50 μg in 50 μl volume of PBS. In addition, an unrelated plasmid DNA (encoding b-galactosidase) injected ID (using the MDD device) was used as negative control. (n=4 animals per group). Luciferase activity in skin was determined as described in Example 1 above.

Figure 2:
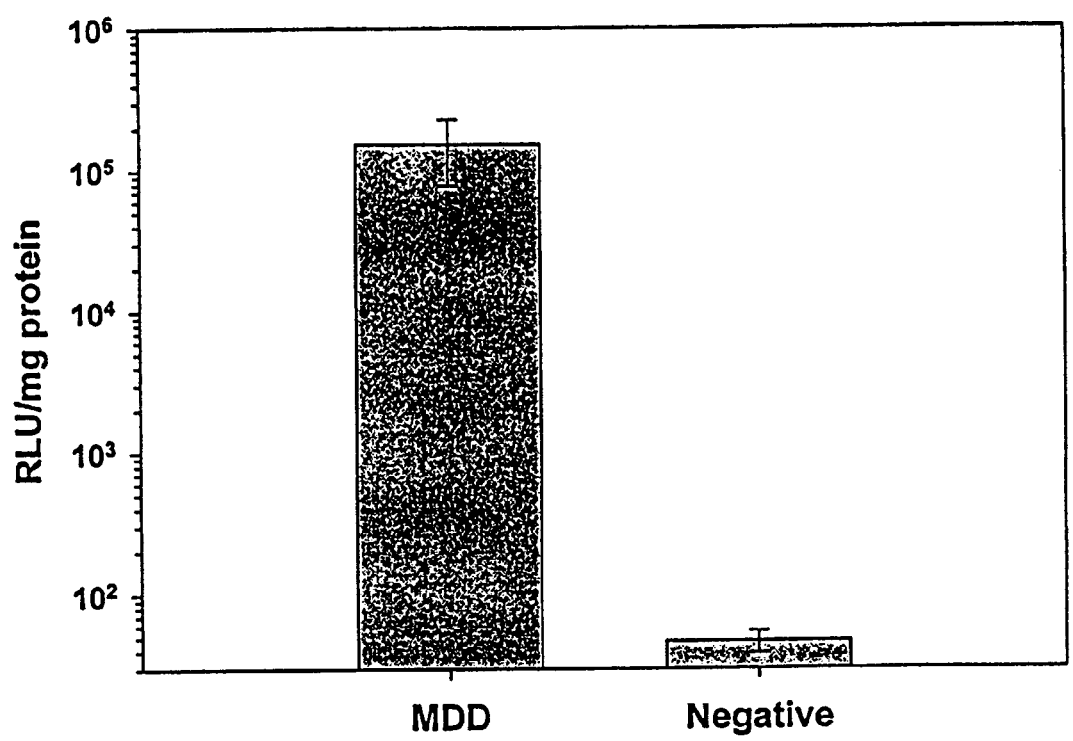
FIG. 2 shows reporter gene activity in rat skin following delivery of plasmid DNA encoding firefly luciferase. Results are shown as RLU/mg protein for intradermal delivery by the microdermal delivery method (one embodiment of the invention, MDD), and control group in which an unrelated plasmid DNA was injected.

The results, shown in FIG. 2, demonstrate very significant geneexpression following ID delivery via the MDD device. Luciferase activity in recovered skin sites was >3000-fold greater than in negative controls. These results further demonstrate the utility of the method of the present invention in delivering gene based entities in vivo, resulting in high levels of gene expression by skin cells.

Example 3

ID Delivery and Expression of Model Genetic Therapeutic/Prophylactic Agents, Pig Model The pig has long been recognized as a preferred animal model for skin based delivery studies. Swine skin is more similar to human skin in total thickness and hair follicle density than is rodent skin. Thus, the pig model (Yorkshire swine; Archer Farms, Belcamp, Md.) was used as a means to predict the utility of this system in humans. Experiments were performed as above in Examples 1 and 2, except using a different reporter gene system, β-galactosidase (Aldevron, Fargo, N. Dak.). Total delivery dose was 50 μg in 50 μl volume. DNA was injected using the following methods I) via Mantoux method using a 30 G needle and syringe, ii) by ID delivery via perpendicular insertion into skin using a 30/31 G needle equipped with a feature to limit the needle penetration depth to 1.5 mm, and iii) by ID delivery via perpendicular insertion into skin using a 34 G needle equipped with a feature to limit the needle penetration depth to 11.0 mm (MDD device). The negative control group consisted of ID delivery by i-iii of an unrelated plasmid DNA encoding firefly luciferase. (n=11 skin sites from 4 pigs for the ID Mantoux group; n=11 skin sites from 4 pigs for ID, 30/31 G, 1.5 mm device; n=10 skin sites from 4 pigs for ID, 34 G, 1 mm device; n=19 skin sites from 4 pigs for negative control.) For the negative control, data from all 3 ID delivery methods were combined since all 3 methods generated comparable results.

Reporter gene activity in tissue was determined essentially as described in Example 1, except substituting the b-galactosidase detection assay (Applied Biosystems, Foster City, Calif.) in place of the luciferase assay.

Figure 3:
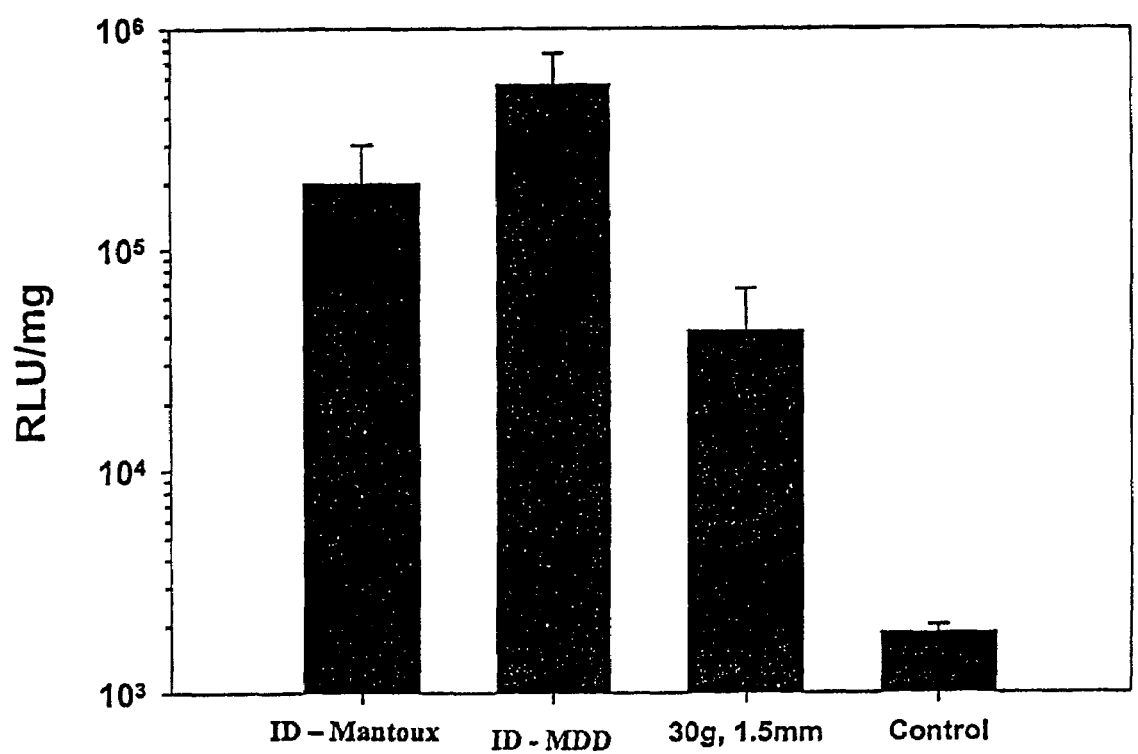
FIG. 3 shows reporter gene activity in pig skin following delivery of plasmid DNA encoding β-galactosidase. Results are shown as RLU/mg protein for intradermal delivery by the Mantoux method, by ID delivery via perpendicular insertion into skin using MDD device (34 g) or 30 g needle to depths of 1 mm and 1.5 mm, respectively, and negative control.

The results, shown in FIG. 3, indicate strong reporter gene expression in skin following all 3 types of ID delivery. Responses in the ID-Mantoux group were 100-fold above background, compared to a 300-fold increase above background in the ID, 34 G, 1 mm (MDD) group and 20-fold increase above background in the ID, 30 G, 1.5 mm (30 g, 1.5 mm) group. Total reporter gene expression by skin cells, as measured by reporter gene mean activity recovered from excised skin tissue biopsies, was strongest in the ID, 34 G, 1 mm (MDD) group at 563,523 RLU/mg compared to 200,788 RLU/mg in the ID, 30 G Mantoux group, 42,470 RLU/mg in the ID (30 G, 1.5 mm) group and 1,869 RLU/mg in the negative controls. Thus, ID delivery via perpendicular insertion of a 34 G, 1.0 mm needle (MDD) results in superior uptake and expression of DNA by skin cells as compared to the standard Mantoux style injection or a similar perpendicular needle insertion and delivery using a longer (1.5 mm), wider diameter (30 G) needle. Similar studies using these 3 devices and methods to deliver visible dyes also demonstrate that the 34 G, 1.0 mm needle results in more consistent delivery to the ID tissue than the other 2 needles/methods and results in less "spill-over" of the administered dose into the subcutaneous (SC) tissue.

These differences were unexpected since all 3 devices and methods theoretically target the same tissue space. However, it is much more difficult to control the depth of delivery using a lateral insertion (Mantoux) technique as compared to a substantially perpendicular insertion technique that is achieved by controlling the length of the cannula via the depth-limiting hub. Further, the depth of needle insertion and exposed height of the needle outlet are important features associated with reproducible ID delivery without SC "spill-over" or leakage on the skin surface.

These results further demonstrate the utility of the methods of the present invention in delivering gene based entities in larger mammals in vivo, resulting in high levels of gene expression by skin cells. In addition, the similarities in skin composition between pigs and humans indicate that comparable clinical improvements should be obtained in humans.

Example 4

Indirect Measurement of Localized Tissue Damage Following ID Delivery

Results presented in Example 3 above suggest that there may be unexpected improvements in efficacy attained by MDD-based ID delivery compared to that attained by Mantoux-based injections using standard needles. In addition, the MDD cannula mechanically disrupt a smaller total area of tissue since they are inserted to a reduced depth compared to standard needles and are not laterally "snaked" through the ID tissue like Mantoux-style injections. Tissue damage and inflammation leads to the release of several inflammatory proteins, chemokines, cytokines and other mediators of inflammation.

Figure 4:
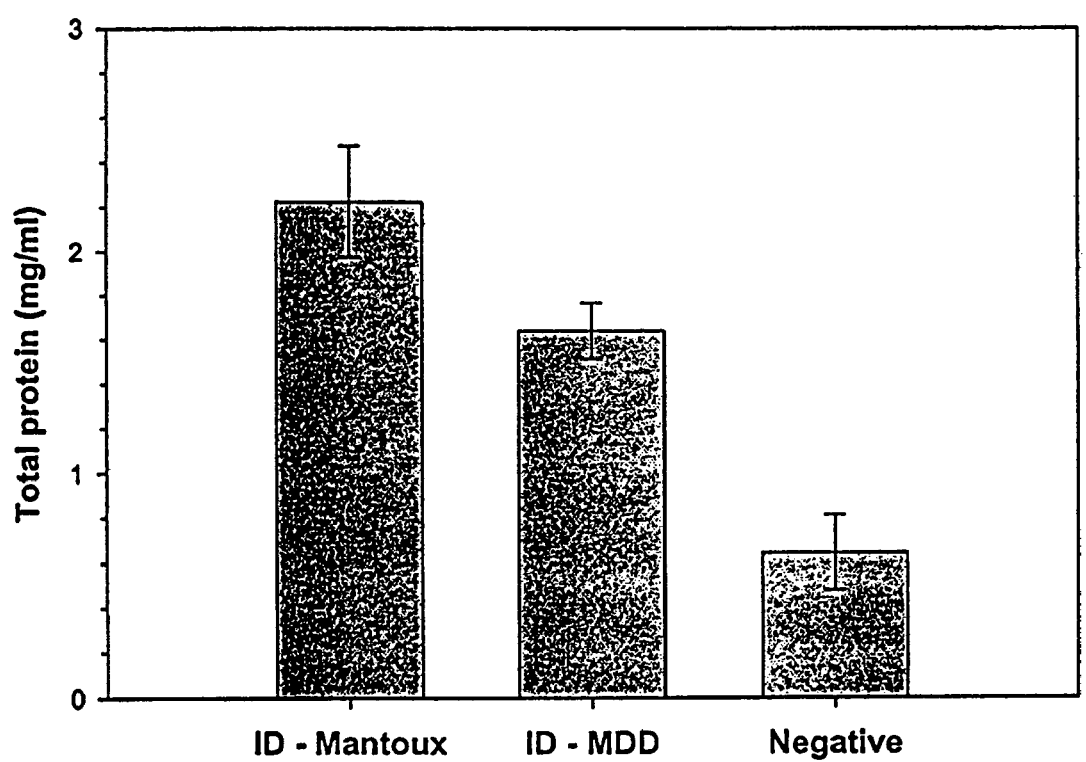
FIG. 4 shows total protein content at recovered skin sites in pigs following Mantoux ID and MDD delivery of reporter plasmid DNA. Control ("Negative") is untreated skin.

Thus, total protein content at recovered skin sites can be used as an indirect measurement of tissue damage and localized inflammation induced by the two delivery methods. Total protein levels were measured in recovered skin biopsies from pig samples presented in Example 3 above (excluding the 30 g, 1.5 mm) using a BCA assay (Pierce, Rockford, Ill.). Both methods of delivery induced an increase in total protein content compared to untreated skin, as shown in FIG. 4. However, total protein levels in recovered skin biopsies from the ID Mantoux group were significantly greater (p=0.01 by t-test) than the corresponding levels in the MDD group (2.4 mg/ml vs. 1.5 mg/ml). These results provide indirect evidence to strongly suggest that delivery by the methods of the present invention induces less mechanical damage to the tissue than the corresponding damage induced by Mantoux-style ID injection.

Example 5

Induction of Immune Response to Influenza DNA Vaccine Following ID Delivery in Rats The examples presented above demonstrate that narrow gauge microcannula can be used to effectively deliver model nucleic acid based compounds into the skin resulting in high levels of gene expression by skin cells. To investigate the utility of delivering DNA vaccines by the methods of the present invention, rats were immunized with plasmid DNA encoding influenza virus hemagglutinin (HA) from strain AIPR/8/34 (plasmid provided by Dr. Harriet Robinson, Emory University School of Medicine, Atlanta, Ga.). Brown-Norway rats (n=3 per group) were immunized three times (days 0, 21 and 42) with plasmid DNA in PBS solution (50 µg per rat in 50 µl volume delivered by rapid bolus injection) ID using the MDD device as described in Example 2 or IM into the quadriceps using a conventional 30 G needle and 1 cc syringe. As a negative control, DNA was applied topically to untreated skin. Sera were collected at weeks 3, 5, 8 and 11 and analyzed for the presence of influenza-specific antibodies by ELISA. Briefly, microtiter wells (Nalge Nunc, Rochester, N.Y.) were coated with 0.1 µg of whole inactivated influenza virus (AIPR/8/34; Charles River SPAFAS, North Franklin, Conn.) overnight at 4° C. After blocking for 1 hr at 37° C. in PBS plus 5% skim milk, plates were incubated with serial dilutions of test sera for 1 hr at 37° C. Plates were then washed and further incubated with horse radish peroxidase conjugated anti-rat IgG, H+L chain (Southern Biotech, Birmingham, Ala.) for 30 min at 37° C. and were then developed using TMB substrate (Sigma, St. Louis, Mo.). Absorbance measurements ($A_{450}$) were read on a Tecan Sunrise™ plate reader (Tecan, RTP, NC).

Figure 5:
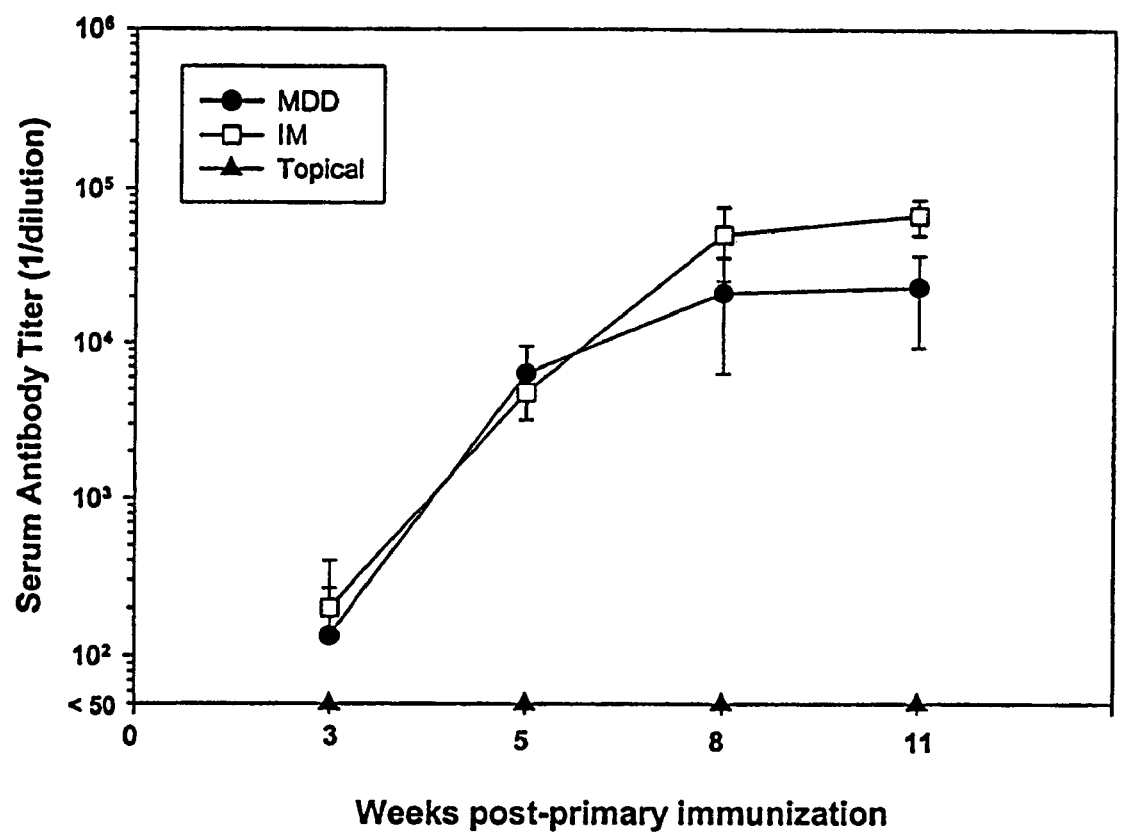
FIG. 5 shows the influenza-specific serum antibody response in rats following delivery of plasmid DNA encoding influenza virus hemagglutinin in the absence of added adjuvant. Plasmid DNA was administered via ID delivery with the MDD device or via intra-muscular (IM) injection with a standard needle and syringe. "Topical" indicates control group, where the preparation was topically applied to skin.

The results (FIG. 5) demonstrate that delivery by the method of the present invention of a genetic influenza vaccine in the absence of added adjuvant induces a potent influenza-specific serum antibody response. The magnitude of this response was comparable to that induced via IM injection at all measured timepoints. No detectable responses were observed in the topical controls. Thus delivery of genetic vaccine by the method of the present invention induces immune responses that are at least as strong as those induced by the conventional route of IM injection.

Figure 6:
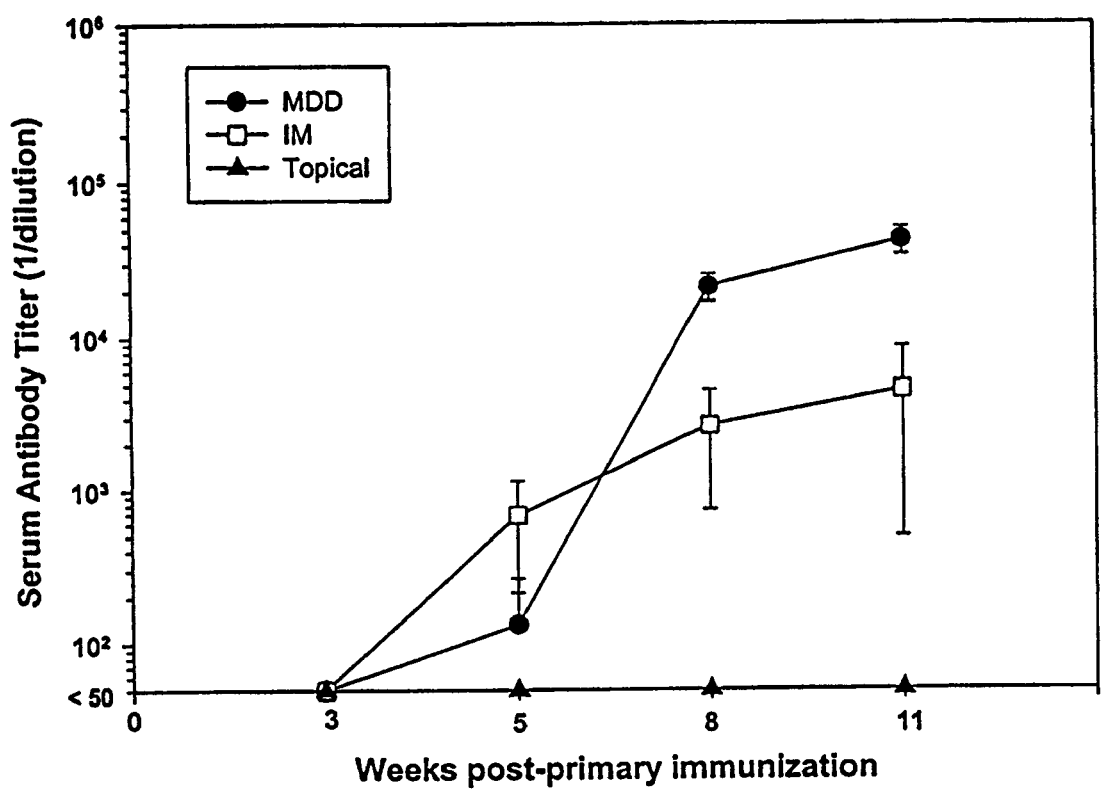
FIG. 6 shows the influenza-specific serum antibody response in rats following delivery of plasmid DNA encoding influenza virus hemagglutinin in the presence of adjuvant. Plasmid DNA was administered via ID delivery with the MDD device or via intra-muscular (IM) injection with a standard needle and syringe. "Topical" indicates control group, where the preparation was topically applied to skin.

To further investigate delivery by the method of the present invention of adjuvanted genetic vaccines, the above described influenza HA-encoding plasmid DNA was prepared using the MPL+TDM Ribi adjuvant system (RIBI Immunochemicals, Hamilton, Mont.) according to the manufacturer's instructions. Rats (n=3 per group) were immunized and analyzed for influenza-specific serum antibody as described above. Titers in the ID delivery group were comparable to IM following the first and second immunization (week 3-5; FIG. 6). After the third dose, however, ID-induced titers were significantly greater (p=0.03 by t-test) than the corresponding titers induced via IM injection (FIG. 6). At week 11, the mean ID-induced titer was 42,000 compared to only 4,600 attained by IM injection. Topical controls failed to generate an influenza-specific response. Thus, delivery by the method of the present invention of genetic vaccines in the presence of adjuvant induces immune responses that are stronger than those induced by the conventional route of IM injection.

Example 6

Induction of Immune Response to Influenza DNA/Virus "Prime-Boost" Following ID Delivery in Rats A recently developed vaccination approach for numerous diseases, including HIV, is the so-called "prime-boost" approach wherein the initial "priming" immunizations and secondary "boosters" employ different vaccine classes (Immunology Today, April 21(4): 163-165, 2000). For example, one may prime with a plasmid DNA version of the vaccine followed by a subsequent boost with a subunit protein, inactivated virus or vectored DNA preparation. To investigate delivery by the method of the present invention of these types of vaccination methods, the first experiment of Example 5 was continued for an additional 6 weeks. At week 11, DNA-primed rats were boosted with whole inactivated influenza virus (A/PR/8/34, 100 µg in 50 µl volume of PBS by rapid bolus injection). Virus was obtained from Charles River SPAFAS, North Franklin, Conn. Influenza-specific serum antibody titers were measured at weeks 13 and 17 by ELISA as described above. Both ID delivery and IM injection induced a potent booster effect (FIG. 7). Week 17 mean influenza-specific titers were equivalent (titer=540,000) by both methods of delivery and were significantly greater than the very weak titers observed following unassisted topical delivery (titer=3200). Thus, delivery by the method of the present invention is suitable for "prime-boost" immunization regimens, inducing immune responses that are at least as strong as those induced by the conventional route of IM injection.

To evaluate the effect of adjuvant on the "prime-boost" response, the second experiment described in Example 5 was continued for an additional 6 weeks. At week 11, DNA-primed rats were boosted with whole inactivated influenza virus (AIPR/8/34, 100 µg in 50 µl volume by rapid bolus injection as above). Influenza-specific serum antibody titers were measured at weeks 13 and 17 by ELISA as described above. Both ID delivery and IM injection induced a potent booster effect (FIG. 8). Mean titers in the ID delivery group were greater than via IM injection following the virus boost; at week 13, the ID-MDD(MDD) mean titer was 540,000 compared to 240,000 by IM injection and 3,200 by unassisted topical application. Thus, delivery by the method of the present invention is suitable for "prime-boost" immunization regimens incorporating adjuvants, inducing immune responses that are stronger than those induced by the conventional route of IM injection.

Example 7

Induction of Immune Response to Influenza Virus Vaccine Following ID Delivery in Rats To investigate the utility of delivering conventional vaccines by the method of the present invention in, rats were immunized with an inactivated influenza virus preparation as described in Example 6 via ID delivery or intramuscular (IM) injection with a standard needle and syringe. As negative control, vaccine solution was applied topically to untreated skin; the large molecular weight of the inactivated influenza virus precludes effective immunization via passive topical absorption. As above, vaccine dose was 100 μg total protein in 50 μl volume per animal delivered by rapid bolus injection (<1 min). Rats were immunized 3 times (days 0, 21 and 42); serum was collected and analyzed for influenza-specific antibodies by ELISA as above on days 21, 35 and 56; n=4 rats per group.

The results, shown in FIG. 9, indicate that ID delivery induces potent antigen specific immune responses. Similar levels of antibody were induced by the 2 injection routes, IM and ID. Peak geometric mean titers were somewhat higher in the ID-MDD group (MDD); 147,200 compared to 102,400 via IM injection. Topical application of the vaccine stimulated only very weak responses (peak mean titer=500). Thus, ID delivery of conventional vaccines at high doses induces immune responses that are at least as strong as those induced by the conventional route of IM injection.

Example 8

Induction of Immune Response to Influenza Vaccine Following ID Delivery Via in Pigs As noted above, the pig represents an attractive skin model that closely mimics human skin. To test ID delivery devices in vaccine delivery, Yorkshire swine were immunized with an inactivated influenza vaccine as above, comparing ID delivery ID with IM injection. Pigs were immunized on days 0, 21 and 49; serum was collected and analyzed for influenza-specific antibodies by ELISA as above on days 14, 36, 49 and 60. Pig-specific secondary antibodies were obtained from Bethyl Laboratories, Montgomery, Tex.

The results (FIG. 10) indicate that ID delivery induces potent antigen specific immune responses. Similar levels of antibody were induced by the 2 injection routes, IM and ID. Peak geometric mean titers were slightly higher in the MDD group; 1,333 compared to 667 via IM injection. Thus, ID delivery of conventional vaccines at high doses induces immune responses that are at least as strong as those induced by the conventional route of IM injection.

Example 9

ID Delivery of Lower Doses of Influenza Vaccine

In Example 7, rats were immunized with 100 μg of inactivated influenza virus via ID injection, or IM using a conventional needle and syringe. At such a high dose, both delivery methods induced similar levels of serum antibodies, although at the last time-point the ID-induced titer was slightly greater than that induced by IM.

To further study the relationship between method of delivery and dosage level, rats were immunized with reduced doses of inactivated influenza virus, ranging from 1 μg to 0.01 μg per animal, using the ID and IM routes of administration as above. Rats were given 3 immunizations (days 0, 21 and 42) and were analyzed for serum anti-influenza antibodies at days 21, 35 and 56 (n=4 rats per group). Data shown in FIG. 11 reflect titers at day 56, although similar trends were observed at day 21 and day 35. ID delivery (MDD) resulted in a significant antibody response that did not differ significantly in magnitude at the 3 doses tested; i.e., delivery of as little as 0.01 μg (long) induced comparable titers to those observed using 100-fold more vaccine (1 μg). In contrast, a significant reduction in titer was observed when the IM dose was reduced from 1 μg to 0.1 μg and again when the dose was further reduced to 0.01 μg. In addition, there was considerably less variability in the titers induced via ID delivery as compared to IM. Notably, no visible side reactions (adverse skin effects) were observed at the ID administration sites.

The results strongly indicate that ID delivery by the method of the present invention enables a significant (at least 100-fold) reduction in vaccine dose as compared to IM injection. Significant immune responses were observed using nanogram quantities of vaccine. Similar benefits would be expected in clinical settings.

The results described herein demonstrate that ID injection of vaccine and genetic material can be reproducibly accomplished the methods of the present invention. This method of delivery is easier to accomplish than standard Mantoux-style injections or IM and, in one embodiment, by virtue of its limited and controlled depth of penetration into the skin, is less invasive and painful. In addition, this method provides more reproducible ID delivery than via Mantoux style injections using conventional needles resulting in improved targeting of skin cells with resultant benefits as described above.

In addition, the method is compatible with whole-inactivated virus vaccine and with DNA plasmids without any associated reduction in biological potency as would occur if the virus particles or plasmid DNA were sheared or degraded when passed through the microcannula at the relatively high pressures associated with ID delivery in vivo. The results detailed herein demonstrate that stronger immune responses are induced via ID delivery, especially at reduced vaccine doses, thus potentially enabling significant dose reductions and combination vaccines in humans.

The results presented above show improved immunization via ID delivery using devices such as those described above as compared to standard intramuscular (IM) injection using a conventional needle and syringe. The dose reduction study (Example 9), shows that ID delivery induces serum antibody responses to an influenza vaccine in rats using at least 100-fold less vaccine than required via IM injection. If applicable in a clinical setting, such dose reduction would reduce or eliminate the problem of influenza vaccine shortages common across the world. In addition, such dose reduction capabilities may enable the delivery of a greater number of vaccine antigens in a single dose, thus enabling combination vaccines. This approach is of particular relevance to HIV vaccines where it likely will be necessary to immunize simultaneously with several genetic variants/sub-strains in order to induce protective immunity.

Similar benefits are expected with other types of prophylactic and therapeutic vaccines, immuno-therapeutics and cell-based entities by virtue of the improved targeting of the immune system using the methods and devices of the present invention.

In another embodiment, it is within the scope of the present invention to combine the ID delivery of the present invention with convention methods of administration, for example IP, IM, intranasal or other mucosal route, or SQ injection, topical, or skin abrasion methods to provide improvement in immunological or therapeutic response. This would include for example, vaccines and or therapeutics of the same or different class, and administration simultaneously or sequentially.

All references cited in this specification are hereby incorporated by reference. The discussion of the references herein is intended merely to summarize the assertions made by their authors and no admission is made that any reference constitutes prior art relevant to patentability. Applicants reserve the right to challenge the accuracy and pertinence of the cited references.

The embodiments illustrated and discussed in the present specification are intended only to teach those skilled in the art the best way known to the inventors to make and use the invention, and should not be considered as limiting the scope of the present invention. The exemplified embodiments of the invention may be modified or varied, and elements added or omitted, without departing from the invention, as appreciated by those skilled in the art in light of the above teachings. It is therefore to be understood that, within the scope of the claims and their equivalents, the invention may be practiced otherwise than as specifically described.

What is claimed is:

1. A method for inducing an immune response to a flaviviral antigen in a human subject comprising delivering a vaccine expressing the flaviviral antigen to a subject's skin using a device that targets the intradermal compartment of the subject's skin, wherein the device comprises at least one hollow microneedle that delivers the vaccine to the subject's skin to a depth of between 0.025 mm and 2.0 mm.

2. A kit for use in inducing an immune response to a flaviviral antigen in a subject, said kit comprising:
   (a) a vaccine expressing the flaviviral antigen; and
   (b) a device that that targets the intradermal compartment of the subject's skin, wherein the device comprises:
      (1) at least one microneedle, wherein the microneedle is supported by a hub potion and has a forward tip that extends away from the hub portion; and
      (2) a limiter portion that surrounds the microneedle and extends away from the hub portion toward the forward tip of the microneedle, wherein the limiter portion comprises a flat skin engaging surface that extends in a plane perpendicular to an axis of the microneedle, the forward tip of the microneedle extending beyond the skin engaging surface at a distance of between 0.5 mm and 2.0 mm.

3. The method of claim 1, wherein the vaccine is a chimeric Japanese Encephalitis vaccine.

4. The method of claim 3, wherein the chimeric Japanese Encephalitis vaccine is JE SA14-14-2.

5. The kit of claim 2, wherein the vaccine is a chimeric Japanese Encephalitis vaccine.

6. The kit of claim 5, wherein the chimeric Japanese Encephalitis vaccine is JE SA14-14-2.

* * * * *